United States Patent [19]
Delaszlo

[11] Patent Number: 6,069,163
[45] Date of Patent: May 30, 2000

[54] AZAPEPTIDE ACIDS AS CELL ADHESION INHIBITORS

[75] Inventor: Stephen E. Delaszlo, Rumson, N.J.

[73] Assignee: Merck & Co., Inc., Rahway, N.J.

[21] Appl. No.: 09/174,631

[22] Filed: Oct. 16, 1998

Related U.S. Application Data

[60] Provisional application No. 60/062,874, Oct. 21, 1997, and provisional application No. 60/065,763, Nov. 17, 1997.

[51] Int. Cl.$^7$ .................. A61K 31/415; A61P 37/08; C07D 231/04
[52] U.S. Cl. .................. 514/403; 314/247; 544/224; 548/356.1
[58] Field of Search .................. 548/356.1; 544/224; 514/403

[56] References Cited

U.S. PATENT DOCUMENTS 4,431,659  2/1984  Sakai et al. .

FOREIGN PATENT DOCUMENTS

| | | |
|---|---|---|
| WO 95/15973 | 6/1995 | WIPO . |
| WO 96/01644 | 1/1996 | WIPO . |
| WO 96/06108 | 2/1996 | WIPO . |
| WO 96/20216 | 7/1996 | WIPO . |
| WO 96/22966 | 8/1996 | WIPO . |
| WO 96/31206 | 10/1996 | WIPO . |
| WO 96/40781 | 12/1996 | WIPO . |
| WO 97/02289 | 1/1997 | WIPO . |
| WO 97/03094 | 1/1997 | WIPO . |

OTHER PUBLICATIONS

Bioorganic & Medicinal Chem Letters vol. 6 No. 21 pp. 2495–2500, 1996.
Med. Chem. 1997, 40, 3359–3368.
Bioorganic Med. Chem. Letter vol. 8, 2297 (1998).

*Primary Examiner*—Robert W. Ramsuer
*Attorney, Agent, or Firm*—Mollie M. Yang; David L. Rose

[57] ABSTRACT

Azapeptide acids of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

22 Claims, No Drawings

AZAPEPTIDE ACIDS AS CELL ADHESION INHIBITORS

CROSS REFERENCE TO RELATED APPLICATIONS

This application is based on, and claims priority from, provisional applications Ser. No. 60/062,874 filed Oct. 21, 1997 and Ser. No. 60/065,763 filed Nov. 17, 1997, both of which are hereby incorporated by reference in their entirety.

BACKGROUND OF THE INVENTION

The present invention relates to novel substituted azapeptide acid derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targeting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, NY, 1996, p. 191).

VLA-4 ("very late antigen-4"; CD49d/CD29; or $\alpha_4\beta_1$) is an integrin expressed on all leukocytes, except platelets and mature neutrophils, and is a key mediator of the cell-cell and cell-matrix interactions of leukocytes (see M. E. Hemler, "VIA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation and on dendritic and macrophage-like cells. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endotlielial cells in response to pro-inflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin ($\alpha_4\beta_1$ (VLA-4) as a therapeutic target" in Cell Adhesion and Human Disease, Ciba Found. Symp., John Wiley & Sons, NY, 1995, p. 79).

$\alpha_4\beta_7$ (also referred to as LPAM-1 and $\alpha_4\beta_1$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their liginds have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leukocyte recruitment and bronchial hyperresponsiveness in the guinea-pig." Eur. J. Pharmacol., 282, 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppi.), 36 95 (1993) and D. Seiffge, "Protective effects of monoclonal antibody to VLA-4 on leukocyte adhesion and course of disease in adjuvant arthritis in rats." J. Rheumatol., 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", J. Clin. Invest., 93, 1700 (1994), A. Jakubowski et al., "Vascular cell adhesion molecule-Ig fusion protein selectively targets activated $\alpha_4$-integrin receptors in vivo: Inhibition of autoimmune diabetes in an adoptive transfer model in nonobese diabetic mice." J. Immunol. 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", Tranplant. Proc., 26, 867 (1994) and S. Molossi et al., "Blockade of very late antigen-4 integrin binding to fibronectin with connecting segment-i peptide reduces accelerated coronary arteripathy in rabbit cardiac allografts." J. Clin Invest., 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", J. Clin. Invest., 92, 372 (1993)); vii) contact hypersensitivity models as a model for skin allergic reactions (see T. A. Ferguson and T. S. Kupper, "Antigen-independent processes in antigen-specific immunity.", J. Immunol., 150, 1172 (1993) and P. L. Chisholm et al., "Monoclonal antibodies to the integrin $\alpha_4$ subunit inhibit the murine contact hypersensitivity response." Eur. J. Immunol., 23, 682 (1993)); viii) acute neurotoxic nephritis (see M. S. Mulligan et al., "Requirements for leukocyte adhesion molecules in nephrotoxic nephritis.", J. Clin. Invest., 91, 577 (1993)); ix) tumor metastasis (for examples, see M. Edward, "Integrins and other adhesion molecules involved in melanocytic tumor progression.", Curr. Opin. Oncol., 7, 185 (1995)); x) experimental autoimmune thyroiditis (see R. W. McMurray et al., "The role of $\alpha_4$ integrin and intercellular adhesion molecule-1 (ICAM-1) in murine experimental autoimmune thyroiditis." Autoimmunity, 23, 9 (1996); and xi) ischemic tissue damage following arterial occlusion in rats (see F. Squadrito et al., "Leukocyte integrin very late antigen-4/vascular ell adhesion molecule-1 adhesion pathway in splanchnic artery occlusion shock." Eur. J. Pharmacol., 318, 153 (1996)). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; atherosclerotic plaque formation; restenosis; and circulatory shock (for examples, see A. A. Postigo et al., "The $\alpha_4\beta_1$/VCAM-1 adhesion pathway in physiology and disease.", Res. Immunol., 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." Immunol. 89, 375 (1996)).

At present, there is a humanized monoclonal antibody (Antegren® Athena Neurosciences/Elan) against VLA-4 in clinical development for the treatment of "flares" associated with multiple sclerosis and a humanized monoclonal antibody (ACT-1® LeukoSite) against $\alpha_4\beta_7$ in clinical development for the treatment of inflammatory bowel disease. Several peptidyl antagonists of VLA-4 have been described (D. Y. Jackson et al., "Potent $\alpha_4\beta_1$ peptide antagonists as, potential anti-inflammatory agents", J. Med. Chem., 40, 3359 (1997); H. N. Shroff et al., "Small peptide inhibitors of $\alpha_4\beta_7$ mediated MadCAM-1 adhesion to lymphocytes", Bioorg. Med. Chem. Lett., 6, 2495 (1996); U.S. Pat. No. 5,510,332, WO97/03094, WO97/02289, WO96/40781, WO96/22966, WO96/20216, WO96/01644, WO96/06108, WO95/15973). There are two reports of nonpeptidyl inhibitors of the ligands for $\alpha_4$-integrins: A. J. Souers et al., "Novel inhibitors of $\alpha_4$b1 integrin receptor interactions through library synthesis and screening", Bioorg. Med. Chem. Lett., 8, 2297 (1998) and (WO96/31206). There still remains a need for low molecular weight, specific inhibitors of VLA-4- and $\alpha_4\beta_7$-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and $\alpha_4\beta_7$ binding and cell adhesion and activation.

SUMMARY OF THE INVENTION

The compounds of the present invention are antagonists of the VLA-4 integrin ("very late antigen-4"; CD49d/CD29; or $\alpha_4\beta_7$) and/or the $\alpha_4\beta_7$ integrin (LPAM-1 and $\alpha_4\beta_p$), thereby blocking the binding of VLA-4 to its various ligands, such as VCAM-1 and regions of fibronectin and/or $\alpha_4\beta_7$ to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or $\alpha_4\beta_7$ binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

DETAILED DESCRIPTION OF THE INVENTION

The present invention provides novel compounds of Formula I

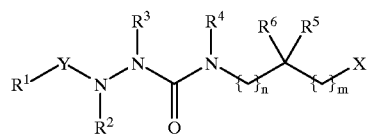

or a pharmaceutically acceptable salt thereof wherein: $R^1$ is

| | |
|---|---|
| 1) | $C_{1-10}$alkyl, |
| 2) | $C_{2-10}$alkenyl, |
| 3) | $C_{2-10}$alkynyl, |
| 4) | Cy, |
| 5) | Cy-$C_{1-10}$alkyl, |
| 6) | Cy-$C_{2-10}$alkenyl, |
| 7) | Cy-$C_{2-10}$alkynyl, | wherein alkyl, alkenyl, and alkynyl are optionally substituted with one to four substituents independently selected from $R^a$; and Cy is optionally substituted with one to four substituents independently selected from $R^b$; $R^2$ and $R^3$ are independently

| | |
|---|---|
| 1) | hydrogen, or |
| 2) | a group selected from $R^1$; or |

$R^2$ and $R^3$ together with the atoms to which they are attached form a ring of 4 to 7 members containing 0–1 additional heteroatoms independently selected from oxygen, sulfur and nitrogen, wherein said ring may be isolated or benzo-fused, and optionally substituted with one to four substituents independently selected from $R^b$; $R^4$ is 1) hydrogen,
2) $C_{1-10}$alkyl,
3) Cy, or
4) Cy-$C_{1-10}$alkyl;

wherein alkyl is optionally substituted with one to four substituents independently selected from $R^a$, and Cy is optionally substituted with one to four substituents independently selected from $R^b$; $R^5$ is selected from the group consisting of 1) hydrogen,
2) $C_{1-10}$alkyl,
3) $C_{2-10}$alkenyl,
4) $C_{2-10}$alkynyl,
5) aryl,
6) aryl $C_{1-10}$alkyl,
7) heteroaryl, and
8) heteroaryl $C_{1-10}$alkyl, wherein alkyl, alkenyl and alkynyl are optionally substituted with one to four substituents independently selected from $R^a$, and aryl and heteroaryl are optionally substituted with one to four substituents independently selected from $R^b$; $R^6$ is 1) hydrogen,
2) $C_{1-10}$alkyl,
3) $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl,
9) $Ar^1$—$Ar^2$—$C_{1-10}$alkyl,
10) $Ar^1$—$Ar^2$—$C_{2-10}$alkenyl,
11) $Ar^1$—$Ar^2$—$C_{2-10}$alkynyl,
12) $Ar^1$—$C_2$alkynyl-$Ar^2$—$C_{1-10}$alkyl,
13) $Ar^1$—$C_2$alkenyl-$Ar^2$—$C_{1-10}$alkyl,
14) $Ar^1$—$Ar^2$, wherein $Ar^1$ and $Ar^2$ are independently aryl or heteroaryl, and each is optionally substituted with one to four substituents independently selected from $R^b$; alkyl, alkenyl and alkynyl are optionally substituted with one to four substituents independently selected from $R^a$; and Cy is optionally substituted with one to four substituents independently selected from $R^b$ except aryl and heteroaryl;
$R^a$ is 1) —$CF_3$;
2) —$OR^d$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$, -continued 15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$, or
21) —$CR^d(N$—$OR^e)$;

$R^b$ is 1) a group selected from $R^a$,
2) $C_{1-10}$ alkyl,
3) $C_{2-10}$ alkenyl,
4) $C_{2-10}$ alkynyl,
5) aryl $C_{1-10}$alkyl,
6) heteroaryl $C_{1-10}$ alkyl,
7) aryl, or
8) heteroaryl;

wherein alkyl, alkenyl, alkynyl, aryl, heteroaryl are optionally substituted with a group independently selected from $R^c$;
$R^c$ is 1) halogen,
2) amino,
3) carboxy,
4) $C_{1-4}$alkyl,
5) $C_{1-4}$alkoxy,
6) hydroxy,
7) aryl,
8) aryl $C_{1-4}$alkyl, or
9) aryloxy;

$R^d$ and $R^e$ are independently selected from the group consisting of 1) hydrogen,
2) $C_{1-10}$alkyl,
3) $C_{2-10}$alkenyl,
4) $C_{2-10}$alkynyl,
5) Cy, and
6) Cy $C_{1-10}$alkyl, wherein alkyl, alkenyl, alkynyl and Cy is optionally substituted with one to four substituents independently selected from $R^c$; or Rd and Re together with the atoms to which they are attached form a heterocyclic ring of 5 to 7 members containing 0–2 additional heteroatoms independently selected from oxygen, sulfur and nitrogen;
$R^f$ and $R^g$ are independently selected from hydrogen, $C_{1-10}$alkyl, Cy and Cy $C_{1-10}$alkyl; or
$R^f$ and $R^g$ together with the carbon to which they are attached form a ring of 5 to 7 members containing 0–2 heteroatoms independently selected from oxygen, sulfur and nitrogen;

1) hydrogen,
2) $C_{1-10}$alkyl,
3) $C_{2-10}$alkenyl,
4) $C_{2-10}$alkynyl,

-continued 5) cyano,
6) aryl,
7) aryl $C_{1-10}$alkyl,
8) heteroaryl,
9) heteroaryl $C_{1-10}$alkyl, or
10) —$SO_2R^i$;

$R^h$ is
wherein alkyl, alkenyl, and alkynyl are optionally substituted with one to four substituents independently selected from $R^a$; and aryl and heteroaryl are each optionally substituted with one to four substituents independently selected from $R^b$;
$R^i$ 1) $C_{1-10}$alkyl,
2) $C_{2-10}$alkenyl,
3) $C_{2-10}$alkynyl, or
4) aryl;

wherein alkyl, alkenyl, alkynyl and aryl are each optionally substituted with one to four substituents independently selected from $R^c$;
Cy is cycloalkyl, heterocyclyl, aryl, or heteroaryl;
m is an integer from 0 to 2;
n is an integer from 0 to 2;
X is 1) —C(O)$OR^d$,
2) —P(O)($OR^d$)($OR^e$)
3) —P(O)($R^d$)($OR^e$)
4) —S(O)$_m$$OR^d$,
5) —C(O)$NR^dR^h$, or
6) -5-tetrazolyl, or
7) $CONHSO_2R^i$;

Y is

1) —C(O)—,
2) —O—C(O)—,
3) —$NR^e$—C(O)—,
4) —S(O)$_2$—,
5) —P(O)($OR^d$)—
6) —C(O)C(O)—.

In one subset of compounds of Formula I, $R^1$ is $C_{1-10}$ alkyl, Cy or Cy-$C_{1-10}$ alkyl wherein alkyl is optionally substituted with one to four substituents independently selected from $R^a$, and Cy is optionally substituted with one to four substituents independently selected from $R^b$. For the purpose of $R^1$ the preferred Cy is aryl or heteroaryl. Examples of suitable $R^1$ are phenyl, 3,5-dichlorophenyl, 3-fluorophenyl, 4-fluorophenyl, benzyl, 4-[(2-methylphenyl)urea]benzyl, t-butyl, benzyl, 3-cyanophenyl, 2-pyridyl, 3-pyridyl, 4-pyridyl, 3-chlorophenyl, 4-(benzamido)phenyl, 4-(phenylacetamido)phenyl and the like.

In another subset of compounds of Formula I, $R^2$ and $R^3$ are independently hydrogen or $C_{1-10}$ alkyl optionally substituted with one to four substituents independently selected from $R^a$, or $R^2$ and $R^3$ together with the atoms to which they are attached form a ring of 5 to 6 members containing 0–1 additional heteroatom selected from the group consisting of oxygen, sulfur and nitrogen, and wherein said ring is optionally substituted with one to four substituents independently selected from $R^b$. Examples of suitable $R^2/R^3$ are hydrogen, butyl, an amino acid side chain which is within the definition of $R^2/R^3$, cyclohexyl, 4-(acetamido)butyl, pyrazolidine, hexahydropyridazine, methylpyrazolidine, and the like.

In another subset of compounds of Formula I, $R^4$ is hydrogen, $C_{1-10}$ alkyl or Cy- $C_{1-10}$ alkyl. Examples of suitable $R^4$ are methyl, benzyl, butyl, hydrogen.

In another subset of compounds of Formula I, $R^5$ is hydrogen and $R^6$ is $C_{1-10}$ alkyl, Cy, Cy-$_{1-10}$ alkyl $Ar^1$-$Ar^2$-, or $Ar^1$-$Ar^2$- $C_{1-10}$alkyl wherein alkyl, Cy, $Ar^1$ and $Ar^2$ are optionally substituted as provided under Formula I. For the purpose of $R^6$ the preferred Cy is aryl or heteroaryl. Examples of suitable $R^6$ are an amino acid side chains which is within the definition of $R^6$, methyl, isobutyl, sec-butyl, benzyl, phenyl, n-butyl, 4-fluorophenyl, naphthyl, biphenylmethyl, 2'-(methoxy)-biphenylmethyl, 2'-(cyano)-biphenylmethyl, 2'-(tetrazol-5-yl)-biphenylmethyl, 2'-(1-methyl-tetrazol-5-yl)-biphenylmethyl, 2'-(2-niethyl-tetrazol-5-yl)-biphenylmethyl, 4-(t-butoxy)-benzyl, biphenyl, 2'-methoxybiphenyl, 2'-cyanobiphenyl and the like.

In another subset of compounds of Formula I, X is —C(O)$OR^d$.

In another subset of compounds of Formula I, Y is —C(O)— or —S(O)$_2$—.

In another subset of compounds of Formula I, n is 0 cr 1 and m is 0 or 1; preferably n+m is 0 or 1.

In a preferred embodiment, the present invention provides a compound of Formula Ia

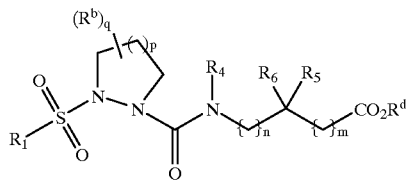

wherein
$R^1$ is

1) $C_{1-10}$alkyl,
2) aryl
3) heteroaryl,
4) aryl-$C_{1-10}$alkyl, or
5) heteroaryl-$C_{1-10}$alkyl, wherein alkyl is optionally substituted with one to four substituents independently selected from $R^a$; and aryl or heteroaryl is optionally substituted with one to four substituents independently selected from $R^b$;
$R^4$ is 1) hydrogen, or
2) $C_{1-10}$alkyl optionally substituted with one to four substituents independently selected from $R^a$;

$R^5$ is hydrogen;
$R^6$ is

| | |
|---|---|
| 1) | $C_{1-10}$alkyl, |
| 2) | aryl, |
| 3) | heteroaryl, |
| 4) | aryl-$C_{1-10}$alkyl, |
| 5) | heteroaryl-$C_{1-10}$alkyl, or |
| 6) | $Ar^1$—$Ar^2$—$C_{1-10}$alkyl, |
| 7) | $Ar^1$—$Ar^2$— | wherein alkyl is optionally substituted with one to four substituents independently selected from $R^a$; aryl or heteroaryl is optionally substituted with one to four substituents independently selected from $R^b$ except aryl and heteroaryl; $Ar^1$ and $Ar^2$ are independently aryl or heteroaryl, and each is optionally substituted with from one to four groups independently selected from $R^b$;
$R^d$ is

| | |
|---|---|
| 1) | hydrogen, |
| 2) | $C_{1-10}$alkyl, |
| 3) | Cy, and |
| 4) | Cy $C_{1-10}$alkyl, | wherein alkyl and Cy are optionally substituted with one to four substituents independently selected from $R^c$;
p is 1 or 2;
q is 0 to 4;
n and m are independently 0 or 1, and n+m=0 or 1;
$R^a$, $R^b$, $R^c$ and Cy are as defined under Formula I.

In a more preferred embodiment, compounds of Formula Ia are provided wherein
$R^1$ is aryl optionally substituted with one to four halogen;
$R^4$ is hydrogen;
$R^5$ is hydrogen;
$R^6$ is

| | |
|---|---|
| 1) | $C_{1-5}$alkyl, |
| 2) | aryl, |
| 3) | aryl-$C_{1-5}$alkyl, or |
| 4) | $Ar^1$—$Ar^2$—$C_{1-5}$alkyl, | wherein alkyl is optionally substituted with one to four substituents independently selected from $R^a$; aryl is optionally substituted with one to four substituents independently selected from $R^b$ except aryl and heteroaryl; $Ar^1$ and $Ar^2$ are independently phenyl, and each is optionally substituted with from one to four groups independently selected from $R^b$.

Representative compounds of Formula I include:

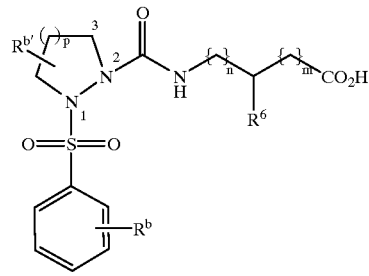

| EX. # | n/m/p | $R^{b'}$ | $R^b$ | $R^6$ |
|---|---|---|---|---|
| 3 | 0/0/1 | H | H | (S)-2-methylpropyl |
| 4 | 0/0/1 | H | 3,5-dichloro | (S)-2-naphthylmethyl |
| 5 | 0/0/1 | (3R)-methyl | 3,5-dichloro | (S)-benzyl |
| 6 | 0/0/1 | (3S)-methyl | 3,5-dichloro | (S)-benzyl |
| 7 | 0/0/1 | 5-methyl | 3,5-dichloro | (S)-benzyl |
| 8 | 0/0/2 | H | 3,5-dichldro | (S)-4-fluorobenzyl |
| 9 | 0/0/2 | H | 3-fluoro | (S)-4-fluorobenzyl |
| 10 | 0/0/1 | H | 3,5-dichloro | (S)-benzyl |
| 11 | 0/0/1 | H | 4-fluoro | (S)-n-butyl |
| 12 | 0/0/1 | H | 4-fluoro | phenyl |
| 13 | 0/0/1 | H | 4-flu6ro | (S)-4'-biphenylmethyl |
| 14 | 0/1/1 | H | 4-fluoro | methyl |
| 15 | 0/1/1 | H | 4-fluoro | benzyl |
| 16 | 0/1/1 | H | 4-fluoro | 2-methylpropyl |
| 17 | 0/1/1 | H | 4-fluoro | phenyl |
| 18 | 1/0/1 | H | 4-fluoro | methyl |
| 19 | 0/0/1 | H | 4-fluoro | (S)-benzyl |
| 21 | 0/0/1 | H | 3-fluoro | (S)-4-fluorobenzyl |
| 22 | 0/0/1 | H | 3-fluoro | (S)-4-(2'-CN-phenyl)benzyl |
| 23 | 0/0/1 | H | 3,5-dichloro | (S)-4-(2'-$CH_3O$-phenyl)benzyl |

-continued

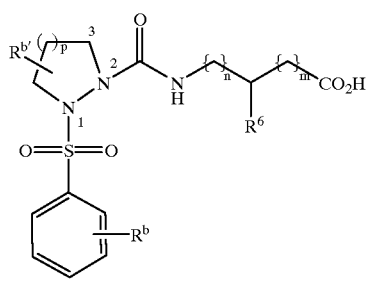

| EX. # | n/m/p | R^b' | R^b | R^6 |
|---|---|---|---|---|

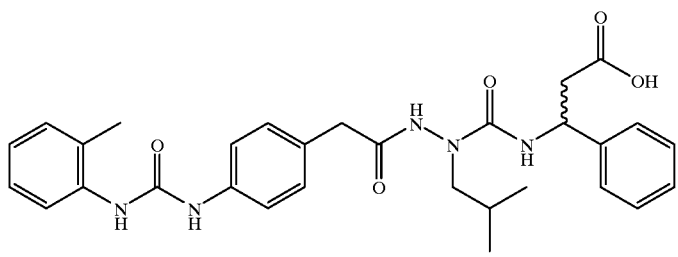

Ex. 1

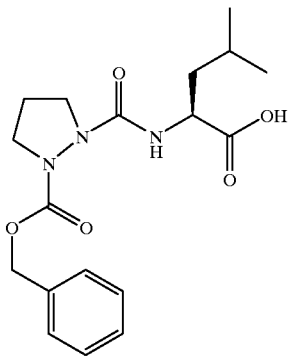

Ex. 2;

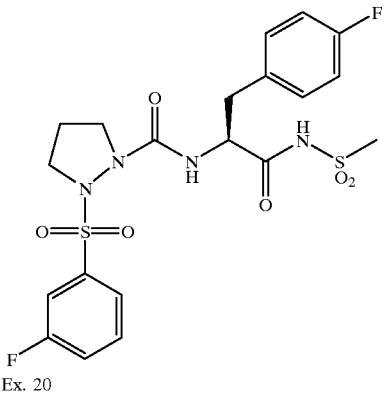

Ex. 20

"Alkyl", as well as other groups having the prefix "alk", such as alkoxy, alkanoyl, means carbon chains which may be linear or branched or combinations thereof. Examples of alkyl groups include methyl, propyl, isopropyl, butyl, sec- and tert-butyl, pentyl, hexyl, heptyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms.

The term also includes monocyclic ring fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like.

"Halogen" includes fluorine, chlorine, bromine and iodine.

Optical Isomers-Diastereomers-Geometric Isomers-Tautomers

Compounds of Formula I contain one or more asymmetric centers and can thus occur as racemates and racemic mixtures, single enantiomers, diastereomeric mixtures and individual diastereoirrers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha_4\beta_7$ integrin makes them useful for preventing or reversing the symptoms, disorders or diseases induced by the binding of VLA-4 and or $\alpha_4\beta_7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression of diseases or disorders or symptoms mediated by VLA-4 and/or $\alpha_4\beta_7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crchn's disease, (15) certain types of toxic and immune-based nephritis, (16) contact dermal hypersensitivity, (17) psoriasis, (18) tumor metastasis, and (19) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 25 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg, of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present inventions suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
| --- | --- |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxepinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxicam), salicylates (acetyl salicylic acid, sulfasalazine) and the pyrazolones (apazone, bezpiperylon, feprazone, mofebutazone, oxyphenbutazone, phenylbutazone); (g) cyclooxygeniase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The synthesis of azapeptides has been reviewed in: J Gante, *Synthesis*, 405–413, 1989. The preparation of azapeptides of Formula I requires the synthesis of suitable regiochemically defined alkyl hydrazine precursors. Alkyl hydrazines are well known to those skilled in the art. A review of the syntheses of alkyl hydrazines may be found by U. Jensen-Korte, *Methoden Org. Chem.* (*Houben-Weyl*) 4th ed. 1952–1990, Vol 16a, pp 421–503.

The method used in this invention is outlined in Scheme 1. tert-butyl carbazate A may be condensed with an appropriate aldehyde or ketone to give, upon reduction by catalytic hydrogenation or treatment with a reducing agent such as borane/THF or sodium cyanoborohydride of the intermediate hydrazone, the protected alkyl hydrazine B. This reagent may be used in the preparation of azapeptides.

Acylation of B with benzylchloroformate (CbzCl) or fluorenylmethylchloroformat? (FMOCCl) gives C which is converted to a regiochemically protected alkyl hydrazine D ready for formation of azapeptides by solution or in the case of the FMOC analog, solid phase technology (vide infra).

It may be necessary to prepare the FMOC analog of B. This material may be prepared by utilizing FMOC-hydrazine in place of A in the sequence A to B. Alternatively, B may be acylated with benzyloxycarbonyl chloride to give E and the Boc group removed by treatment with trifluoroacetic acid (TFA) to give F. Acylation of F with FMOCCl followed by hydrogenation over palladium and carbon gives G.

1,2-Dialkyl hydrazine syntheses are described in U. Jensen-Korte, *Methoden Org. Chem.* (*Houben-Weyl*) 4th ed. 1952–1990, Vol 16a, pp 503–529. In the case of symmetrical 1,2-dialkyl hydrazines ($R^2$ equal to $R^3$) protection of one of the two nitrogen atoms may not be necessary for the syntheses of azapeptides in a regiochemically defined manner. In the case of unsymmetrical 1,2-dialkyl regiochemically protected hydrazines may be prepared by the approach outlined in Scheme 1.

The intermediate E may be alkylated in the presence of a base such as sodium hydride and an alkylating agent to give H. Hydrogenolysis of the Cbz group would produce the regiochemically defined protected unsymmetrical hydrazine I. Protecting group manipulation under standard conditions may then provide other suitably protected unsymmetrical hydrazines J. Alternatively, intermediate F may be reductively alkylated with an aldehyde or ketone to give K. K may also be derived from H by treatment with an acid such as TFA. Protecting group manipulation may then give regiochemically defined protected unsymmetrical hydrazine L.

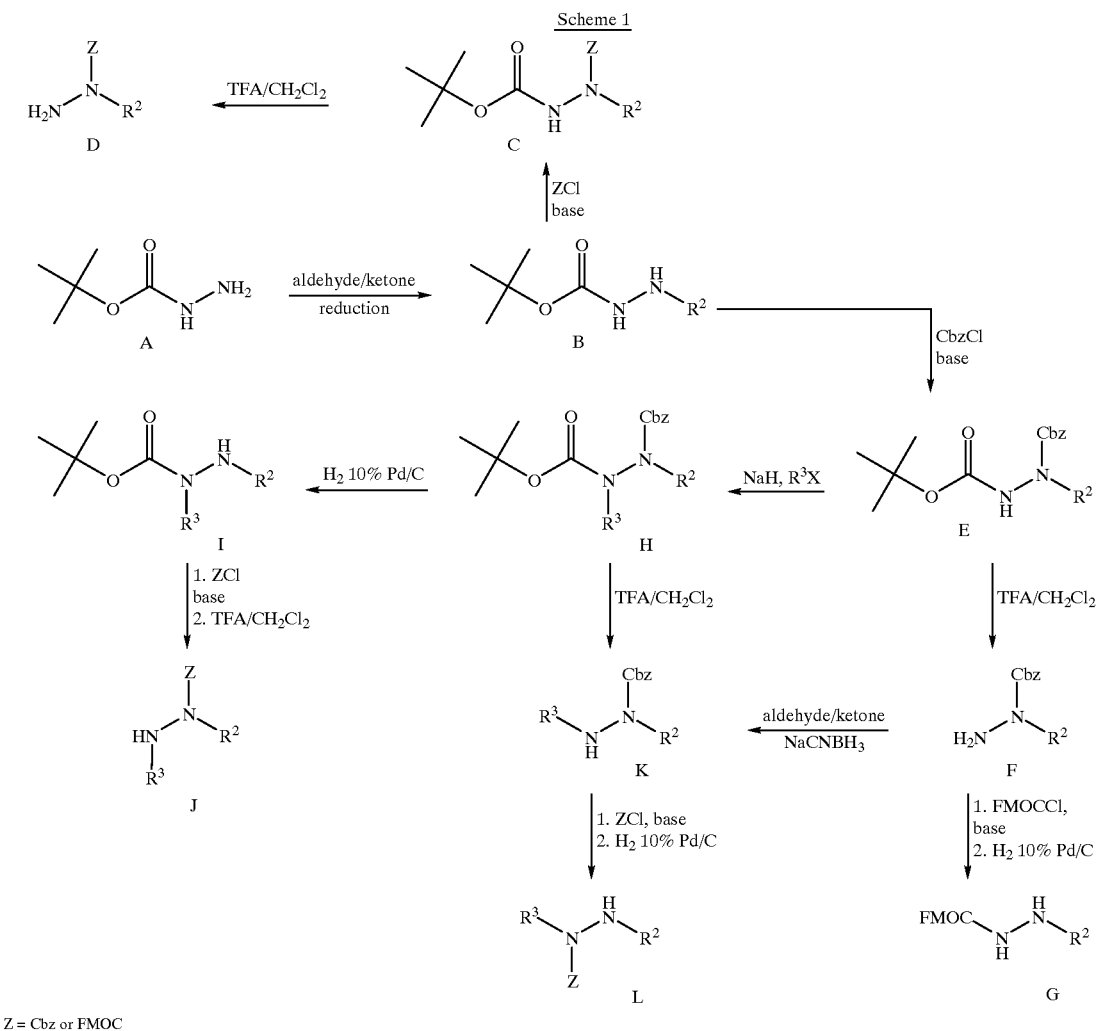

Methods that provide cyclic hydrazines ($R^2$ and $R^3$ are linked) are outlined in Schemes 2 and 3, below. General methods for the synthesis of such compounds are outlined in U. Jensen-Korte, *Methoden Org. Chem.* (*Houben-Weyl*) 4th ed. 1952–1990, Vol 16a, pp 503–529 and *J. C. S. Perkin* 1 1712–1720 1975. tert-butyl carbazate A is converted to the Cbz protected diacylhydrazide B. Dialkylation of B with a dibromoalkane (as required for the appropriate ring size) gives C. The Cbz group of C is removed by hydrogenolysis and the resulting intermediate D may be used in azapeptide formation. Treatment of D with hydrogen chloride provides E, another useful intermediate for solution or solid phase azapeptide synthesis. The FMOC analog of E, for use in solid phase synthesis, may be prepared from D by acylation followed by Boc deprotection under standard conditions to give F. An alternative method of preparing E in a more direct fashion is vial the di-Boc cyclic hydrazine G that is in turn prepared from the di-Boc-hydrazine H as shown below. In the case of benzofused rings the appropriate alkylating reagents are used. Alkylating agents incorporating other heteroatoms (0, N(protected), S), would provide cyclic hydrazines with additional heteroatoms in the ring.

substituted dibromoalkane provides a mixture of regioisomeric diacyl pyrazolidines. This mixture may be separable. In the event that separation may not be achieved, treatment of the mixture with TFA may give rise to a separable mixture of monoacyl pyrazolidines B and C. The monoacyl pyrazolidines may subsequently bib utilized in the preparation of azapeptides in solution phase, or alternatively, following

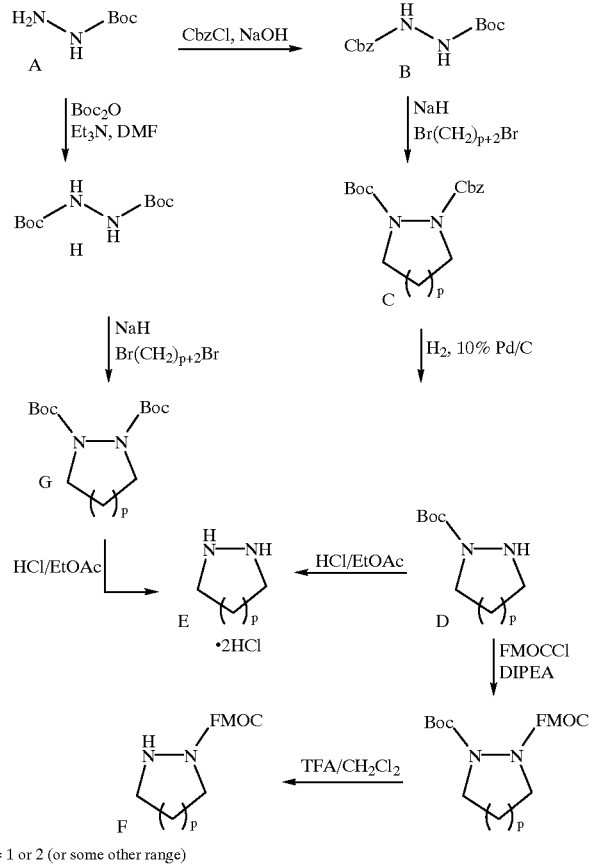

Unsymmetrical substituted pyrazolidines may be prepared as described in Scheme 3. Dialkylation of A with a functional group manipulation solid phase technology may be utilized.

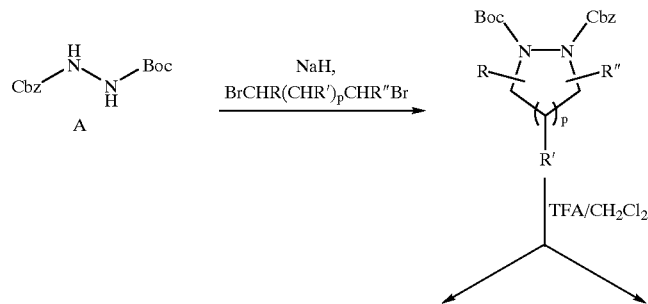

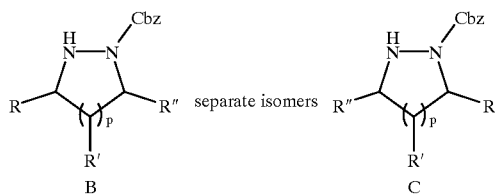

R, R', R" = alkyl, aryl, heteroaryl, hydrogen
p = 1, 2

The structure of azapeptides of Formula I are characterized by the presence of a key urea bond as seen in A Scheme 4. The synthesis of the intermediates toward Formula I is outlined in Scheme 4. The protected hydrazine B is reacted with an equivalent of an activating agent such as phosgene (or triphosgene), p-nitrophenylchloroformate or carbonyl duimidazole in the presence of a base such a triethylamine or duisopropylethylamine to give an intermediate of structure C. Addition of a suitably protected amino acid D (protecting groups such as a tert-butyl ester for a carboxylic acid are preferred; however the X group may also be unprotected in the case of initial activation of the hydrazine) may provide compounds of structure A. Alternatively, the amino a(id D may be activated to give E which in turn may be combined with B to give A. Removal of the protecting group is, in general, the next step to provide a monoacylhydrazine F ready for attachment of the $R^1Y$ group and may be accomplished under conditions appropriate to the protecting group being utilized. The use of a hydrazine protecting group may be avoided by addition of the unprotected hydrazine G directly to the activated amino acid E (preferably $R^2=R^3$ or is cyclic, to avoid formation of regioisomeric mixtures).

Scheme 4

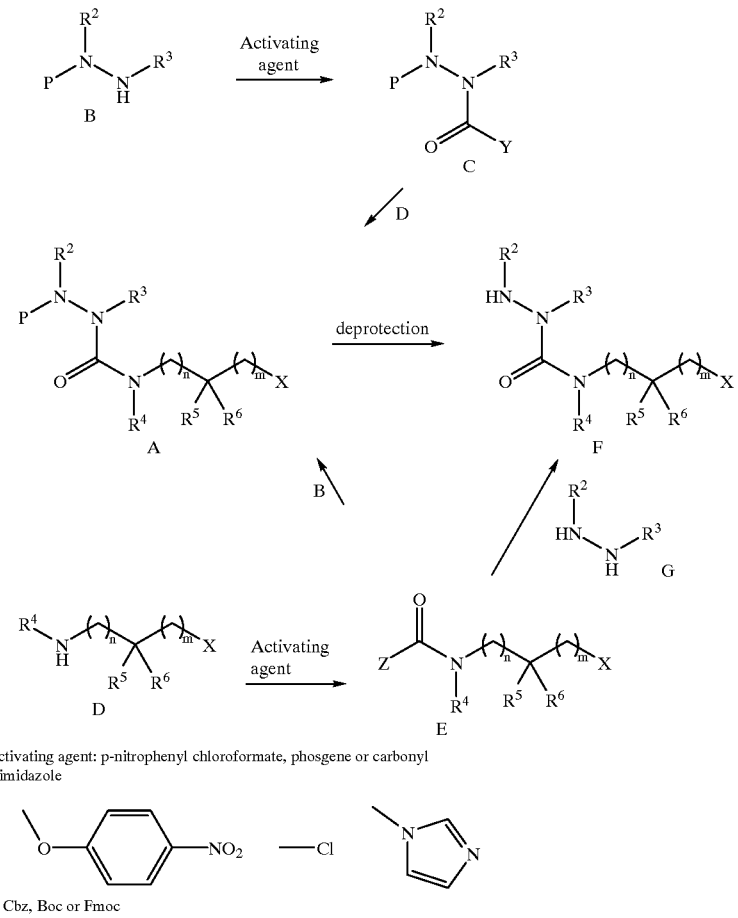

Attachment of the $R^1$ group follows, utilizing methods known to one skilled in the art. Reaction of the acylhydrazide A in Scheme 5 with the activated mixed anhydride of an R¹ carboxylic acid gives the amide B. Reaction of A with an appropriately substituted sulfonyl chloride, glyoxyl chloride, phosphinyl chloride or chloroformate gives the corresponding product C. Reaction of A with an isocyanate, or by utilizing chemistry outlined in Scheme 4 provides ureas D. Further Y group may be introduced by reaction of the requisite glyoxyl chloride, phosphinyl chloride, or chloroformate. Compounds of Formula I may then be prepared by removal of any protecting groups of the acid function X by utilization of methods known to those skilled in the art (for example in the case of X=COOtBu, treatment with TFA in CH$_2$Cl$_2$ will give X=COOH).

resin B. The resulting resins are treated with 20% piperidine/ dimethylformamide (DMF) several times and are then washed with DMF several times followed by the solvent for the next reaction to give C. Treatment of the resin with an excess of an activating agent such as p-nitrophenylchloroformate or phosgene or an equivalent thereof will produce the intermediate D. Addition of an FMOC protected hydrazine and a tertiary amine base such as diisoproylethylamine or the unprotected hydrazine and diisopropylethylamine (if R$^2$=R$^3$) will give E and F respectively. Activation of the hydrazine by treatment with triph- Scheme 5

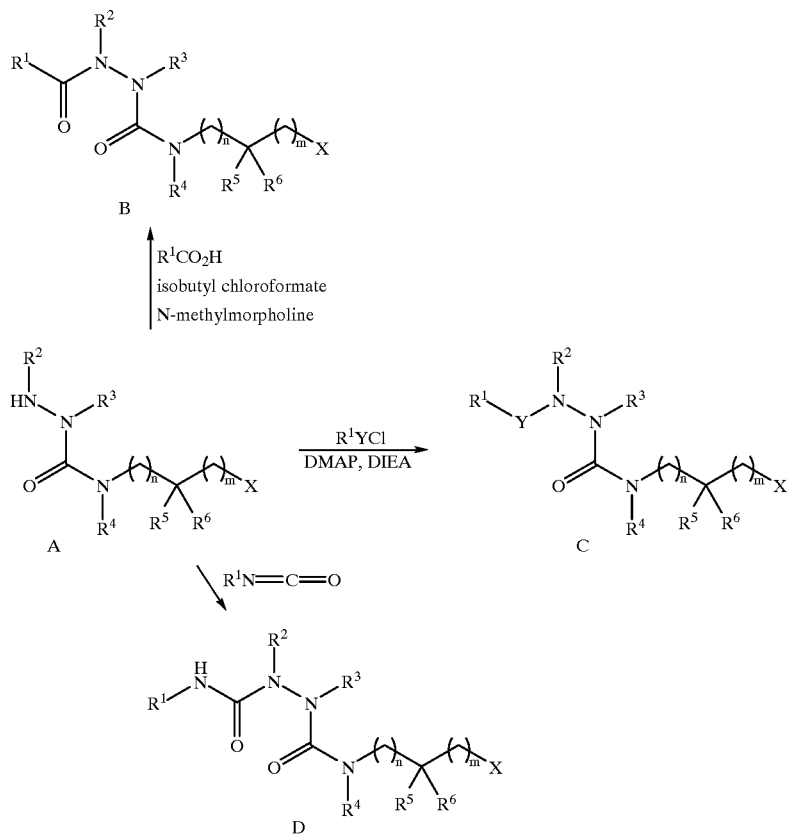

Compounds of Formula I may also be prepared on polystyrene supports, as shown in Scheme 6, thereby permitting the rapid synthesis of analogs through the use of excess reagents to drive reactions to completion and filtration to remove reagents from the resin and the attached products. FMOC protected amino acids A are coupled to an appropriate acid sensitive linker such as 4-hydroxymethyl-3-methoxyphenol which is, in turn, attached to the polystyrene osgene and a tertiary amine base followed by addition of this reagent in excess to the resin may give the acyl hydrazine E. Addition of 20% piperidine/DMF leads to conversion of E into F. Acylation of the acyl hydrazine in the presence of dimethylaminopyridine and a tertiary amine base gives the penultimate intermediate G. Thorough washing of the resin is followed by acid catalyzed cleavage (for example 10% trifluoroacetic acid in methylene chloride) of the product of Formula I (where X is CO2H) from the resin.

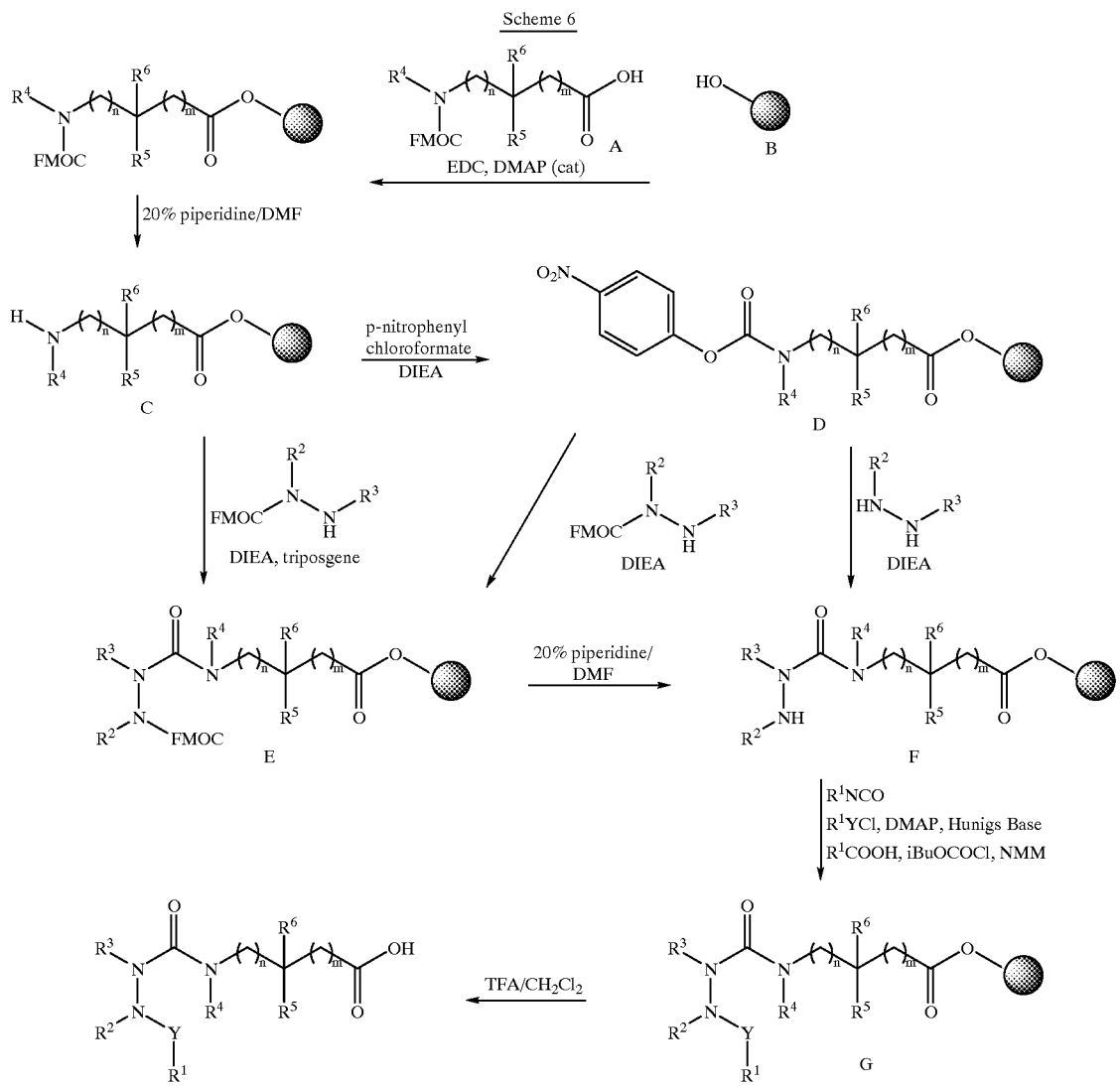

Scheme 6

Compounds wherein $R^6$ has a biaryl moiety may be prepared as outlined in Scheme 7. Substituted aryl or heteroaryl boronic acids are coupled to A in the presence of a palladium(0) reagent, such as tetrakis(triphenylphosphine) palladium under Suzuki conditions (N. Miyaura et al., *Synth. Commun.*, 1981, 11, 513–519) to yield B. Tyrosine triflate starting materials are prepared by treatment of the tyrosine analog of A with triflic anhydride in pyridine. The protecting group is then removed to give the corresponding compounds of Formula I. If the aryl or heteroaryl boronic acid is not commercially available, but the corresponding bromide or iodide is, then the bromide or iodide can be converted into the desired boronic acid by treatment with an allkyllithium reagent in tetrahydrofuran at low temperature followed by addition of trimethyl or triusopropyl borate. Hydrolysis to the boronic acid can be effected by treatment of the intermediate with aqueous base and then acid. aryl boronates which may also be utilized in coupling reactions in place of aryl boronic acids may be prepared by palladium catalyzed boronation of aryl iodides and bromides as described in J. Org Chem, 1995, 60, 7508–7510.

Scheme 7

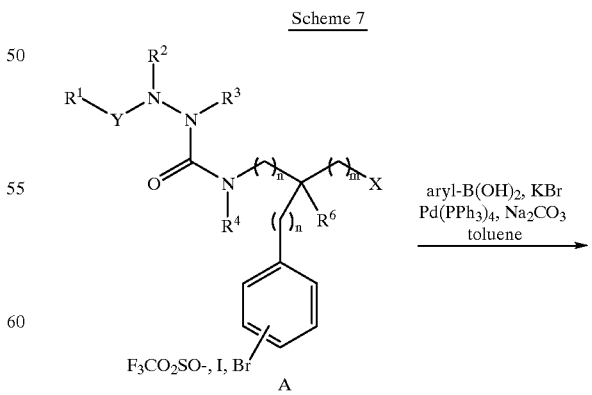

29

-continued

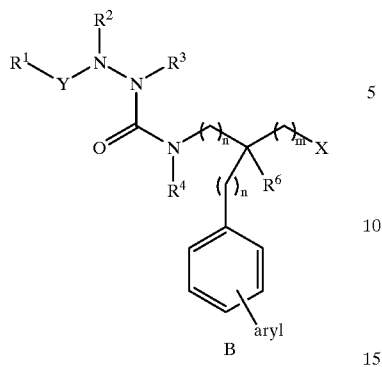

B

Alternatively, the aryl coupling reaction may be performed by application of Stille-type carbon-carbon bond forming conditions (Scheme 8). (A. M. Echavarren and J. K. Stille, *J. Am. Chem. Soc.* 1987, 109, 5478–5486). The aryl bromide or iodide intermediate A is converted into its trimethyltin derivative B using hexamethylditin in the presence of palladium(O) and lithium chloride and then reacted with an appropriately substituted aryl or heteroaryl bromide, iodide, or triflate in the presence of a palladium reagent, such as tetrakis(triphenylphosphine)palladium(0) or tris(dibenzylideneacetone)dipalladium(0), in a suitable solvent, such as toluene, dioxane, dimethylformamide (DMF), or 1-methyl-2-pyrrolidinone, to give intermediate C. The protecting group is then removed to give compounds of Formula I.

Scheme 8

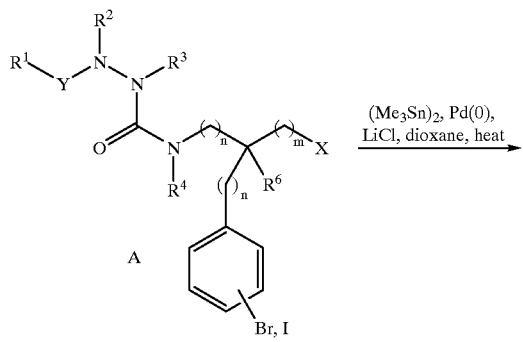

30

-continued

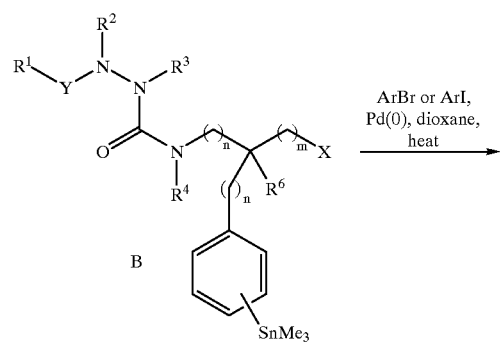

The following Examples are provided to illustrate the invention and are not to be construed as limiting the invention in any manner.

EXAMPLE 1

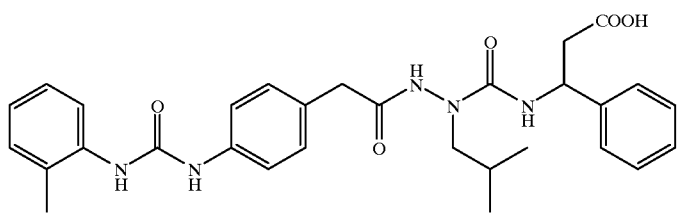

Step A. Preparation of N-Boc-N'-isobutyl hydrazine 10.0 g (75 mmol) of tert-butyl carbazate was combined with 5.46 g (75 mmol) of isobutyraldehyde in 100 mL of THF. The reaction mixture was stirred under nitrogen overnight and concentrated in vacuo. Hexanes were added and the material was triturated to give a white precipitate of N-Boc-N'-isobutyl imine. 1.0 g (5.3 mmol) of the imine was dissolved in 5 mL of THF at room temperature. To this solution 393 mg (5.3 mmol) of sodium cyanoborohydride was added in 5 mL of THF. A solution of 1.02 g (5.3 mmol) of p-toluenesulfonic acid was added in 5 mL of THF. The reaction mixture was stirred overnight. 20 mL of 1N NaOH solution was added portionwise and the reaction mixture was extracted with 50 mL of ethyl acetate (EtOAc). The organic phase was washed with saturated sodium bicarbonate and brine and was dried over $MgSO_4$. The mixture was filtered and concentrated in vacuo to give the desired product. $^1$H-NMR ($CDCl_3$): 0.9 (d, 6H); 1.43 (s, 9H); 1.7 (m, 1H); 2.63 (d, 2H).

Step B. Preparation of:

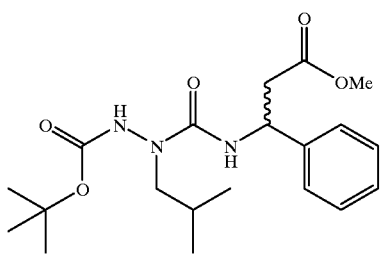

To a solution of 1.0 g (5.3 mmol) of the product of Step A in 10 mL of $CH_2Cl_2$ was added 1.37 g (10.6 mmol) of diisopropylethylamine. The solution was cooled to 0° C. at which time 0.53 g (1.8 mmol) of triphosgene was added as a solid. A solution of methyl 3-amino-3-phenyl-propionate (1.0 g, 5.6 mmol) in 8 mL of $CH_2Cl_2$ was added dropwise. After 30 minutes a further 4 molar equivalents of diisopropylethylamine was added and the reaction mixture was stirred at room temperature over night. The reaction mixture was diluted with ethyl acetate and washed with water and brine and was dried over $MgSO_4$. The product was purified by silica gel flash chromatography eluting with 30% ethyl acetate hexanes to give the product as a gum. FABMS: Calculated $M^+$=293, Obs $M^+$+1: 294.2, $^1$H-NMR ($CD_3OD$): 0.9 (d, 6H); 1.5 (s, 9H); 1.85 (m, 1H); 2.87 (m, 4H); 3.6 (s, 3H); 5.2 (d, 111); 7.1–7.4 (m, 5H).

Step C. Preparation of:

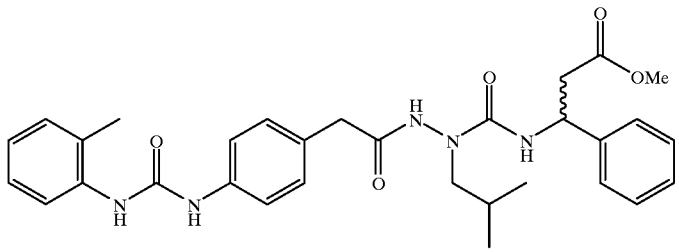

The product of Step B was dissolved in 8.0 mL of 50% trifluoroacetic acid/$CH_2Cl_2$ and stirred at room temperature for 1 L hour. The reaction mixture was concentrated in vacuo. To a solution of 73 mg (0.25 mmol) of o-methyl-phenylureaphenylacetic acid (prepared as in International Patent Application WO 96/22966) dissolved in a mixture of 1 mL of THF and 2 mL of DMF and 25 mg (0.25 mmol) of N-methyl morpholine at −15° C was added 34 mg of isobutylchloroformate. After 15 minutes a solution of 34 mg (0.25 mmol) of the TFA treated material above in 2 mL of THF was added. The reaction mixture was stirred at −15° C. for 30 minutes and then at room temperature for 3 hours. On addition of a mixture of 10 mL of EtOAc/$CH_2Cl_2$ a precipitate formed that was collected by filtration and was washed with 10 mL of EtOAc/$CH_2Cl_2$ to give the desired product. FABMS: Calculated $M^+$=559, Obs $M^+$+1: 560.2 (M+H), 577.2 ($M^+$+H+$NH_3$), $^1$H-NMR ($CD_3OD$): 0.85 (m, 6H); 1.75 (m, 1H); 2.3 (s, 3H); 2.8 (d, 2H); 3.55 (s, 2H); 3.6 (s, 3H); 5.2 (m, 1H); 6.73 (d, 1H); 7.1 (t, 1H); 7.1–7.3 (m, 8H); 7.45 (d, 2H); 7.62 (d, 1H).

Step D. Synthesis of the title compound

To a solution of 30 mg (0.054 mmol) of the product of Step C in 1 mL of MeOH was added 0.016 mL of a 5N NaOH solution in water (0.081 mmol). The reaction mixture was stirred at room temperature over night. The solution was acidified to pH 2.0, diluted with water and filtered. The solid was washed with ether to provide the desired. product. 10 FABMS: Calculated $M^+$=545, Obs $M^+$+1: 546.2 (M+H), 560.2 ($M^+$+H+$NH_3$), $^1$H-NMR ($CD_3OD$): 0.85 (m, 6H); 1.75 (m, 1H); 2.3,: (s, 3H); 2.75 (m, 2H); 3.35 (s, 2H); 3.53 (s, 2H); 3.6 (s, 1H); 5.15 (m, 1H); 7.05 (t, 1H); 7.1–7.3 (m, 9H); 7.42 (d, 2H); 7.65 (d, 1H).

EXAMPLE 2

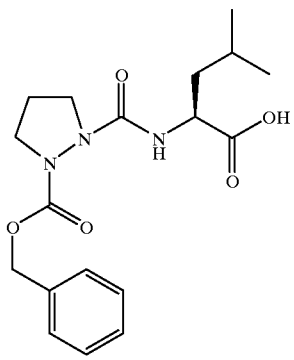

Step A. Preparation of 1-benzyloxycarbonyl-2-t-butoxycarbonylhydrazine.

5.5 g (41.6 mmol) of tert-butyl carbazate was dissolved in a mixture of 60 mL of $CHCl_3$ and 20 mL of water. 1.87 g (47 mmol) of sodium hydroxide was added and the solution was cooled to 0° C. 5.9 g (41.6 mmol) of benzyl chloroformate was added dropwise neat and the reaction mixture was stirred over night allowing the temperature to rise to room temperature. The organic phase was separated and washed with 5% citric acid solution, water and brine and was dried over MgSO$_4$.

The mixture was filtered and concentrated in vacuo to give the product as a crystalline solid following recrystallization from 20% EtOAc/hexanes. $^1$H-NMR (400 MHz, CDCl$_3$): 1.5 (s,9H); 5.1(s,2H); 6.2 (bs,1H); 6.5 (bs,1H); 7.3 (m,5H).

Step B. Preparation of 1-benzyloxycarbonyl-2-t-butoxycarbonylpyrazolidine 3.0 g (75 mmol) of 60% sodium hydride in oil was suspended in 50 mL of DMF. 10 g (37.5 mmol) of 1-benzyloxycarbonyl-2-t-butoxycarbonylhydrazine was added in 50 mL of DMF dropwise to the mixture. The reaction mixture was stirred at room temperature for 1 hour and then 3.8 mL (37.5 mmol) of 1,3-dibromopropane was added. The reaction mixture was stirred over 48 hours and the solvent was then removed in vacuo. The residue was dissolved in ethyl acetate and washed successively with 5% aqueous citric acid solution, saturated sodium carbonate solution, water and brine and was dried over MgSO$_4$. The mixture was filtered and concentrated in vacuo to give the desired product. $^1$H-NMR (400 MHz, CDCl$_3$): 1.4 (s,9H); 2.1 (m,2H); 3.3 (m,1H); 3.4 (m,1H); 3.8 (bs, 2H); 5.1(bd, 1H); 5.3 (bd, 1H), 7.4 (m,5H).

Step C. Preparation of 1-benzyloxycarbonyl-pyrazolidine, trifluoroacetic acid salt.

2.4 g (7.8 mmol) of 1-benzyloxycarbonyl-2-t-butoxycarbonylpyrazolidine was dissolved in 20 mL of 25% trifluoroacetic acid/CH$_2$Cl$_2$ at room temperature. The solution was stirred for 4 hours and concentrated in vacuo to give a gum. $^1$H-NMR (400 MHz, CDCl$_3$): 2.4 (q, 2H); 3.7 (t, 2H); 3.8 (t,2H); 5.2 (s, 2H); 7.28–7.35 (m, 5H).

Step D. Preparation of benzyloxycarbonyl-α-aza-prolyl-(L)-leucine, tert-butyl ester.

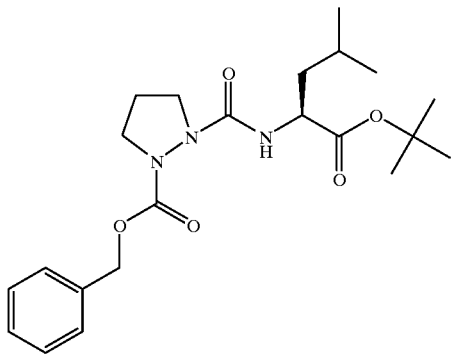

0.5 g (1.56 mmol) of the product of Step C was dissolved in 7 mL of CH$_2$Cl$_2$ to which was added 1.1 mL (6.24 mmol) of diIsopropylethylamine. The reaction mixture was cooled to 0° C. and 0.15 g (0.5 mmol) of triphosgene was added. The reaction mixture was stirred for 30 minutes at which time a solution of 0.35 g (1.56 mmol) of L-leucine tert-butyl ester was added in 5 mL of methylene chloride and 1.1 mL (6.24 mmol) of diisopropylethylamine. The reaction mixture was stirred at room temperature over night and then was then diluted with 25 mL of ethyl acetate. The solution was washed with 5% citric acid, water and brine and was dried over MgSO$_4$. The mixture was filtered and concentrated in vacuo. The residue was purified by silica gel flash chromatography eluting with 40% EtOAc/hexanes to give the desired product as a gum. $^1$H-NMR (400 MHz, CDCl$_3$): 0.8–0.9 (dd, 6H); 1.4 (s, 9H);1.4–1.7 (bm, 3H); 2.0 (m, 2H); 3.0–4.0 (v.bm, 4H); 4.3 (m, 1H); 5.2(m, 2H); 5.9(d,1H); 7.2–7.4 (m, 5H).

Step E. Preparation of benzyloxycarbonyl-α-aza-prolyl-(L)-leucine.

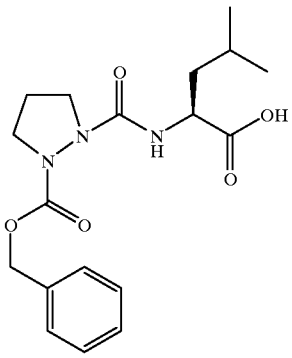

0.05 g (0.11 mmol) of the product of Step D was dissolved in 0.5 mL of CH$_2$Cl$_2$ to which was added 0.055 mL of trifluoroacetic acid. The reaction mixture was stirred over night at room temperature and was then concentrated in vacuo. The residue was purified by preparative thin layer chromatography over silica gel eluting with 70% EtOAc/hexanes to provide the desired product as a gum. FABMS: Calculated M$^+$=363.18 Obs M$^+$+H$^+$=364.2, M$^+$+H$^1$+NH$_3$= 381.1. H-NMR (400 MHz, 1H):0.85(dd, 6H); 1.4(m, 2H); 1.5–1.6(m, 3H); 2.0(m, 2H); 3.0–4.0(bm, 2H); 4.4(m, 1H); 5.2(dd, 2H); 5.9(d, 1H); 7.3–7.4(m, 5H).

EXAMPLE 3

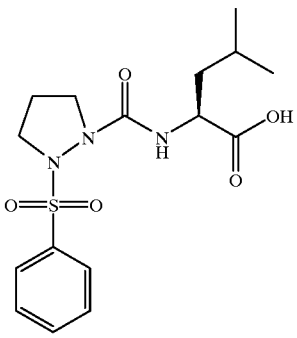

Step A. Preparation of α-aza-prolyl-(L)-leucine, tert-butyl ester.

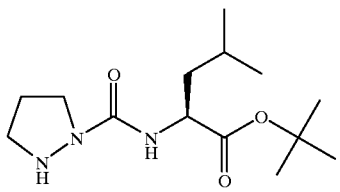

143 mg (0.34 mmol) of the product of Example 2, Step D was dissolved in 20 mL of methanol. A catalytic amount of 10% Pd/C was added and the reaction mixture was stirred under an atmosphere of hydrogen gas over night. The reaction mixture was filtered through celite and concentrated in vacuo to give the desired product as a gum. H-NMR (400 MHz, CDCl$_3$): 0.9 (d,3H); 0.92(d,3H); 1.4(s,9H); 1.5(m, 1H); 1.6(m,1H), 1.7(m, 1H); 2.0 (bm,2H); 2.9(bm 2H); 3.4(bm,1H); 3.5(bm,1H); 3.7(t, 1H); 4.3(m,1H); 6.6(d,1H).

Step B. Preparation of N-phenylsulfonyl-α-aza-prolyl-(L)-leucine, tert-butyl ester

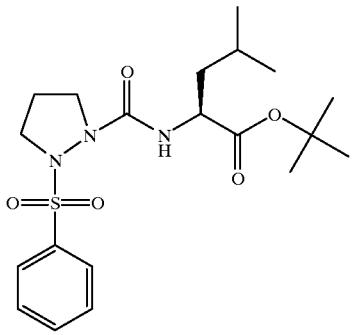

A solution of 0.115 g (0.4 mmol) of the product of Step A in 2.0 mL of $CH_2Cl_2$ was treated with 0.085 mL (0.48 mmol) of diisopropyl ethyl amine, 0.062 mL (0.48 mmol) of phenylsulfonyl chloride and 10 mg of dimethyaminopyridine. The reaction mixture was stirred at room temperature over 3 days, diluted with methylene chloride and washed successively with 1N HCl, water and brine. The solution was dried over $MgSO_4$, filtered and concentrated in vacuo to give, following purification by preparative thin layer chromatography over silica gel, eluting, with 70% EtOAc/hexanes, the desired product. H-NMR (400 MHz, $CDCl_3$): 0.91(d,3H); 0.92(d,3H); 1.47(s,9H); 1.5(m,1H); 1.6(m,1H); 1.7(m,1H); 1.8(m,1H); 2.4(m,1H); 3.4(m,1H); 3.8(m,1H); 3.9(m,1H); 4.3(m,1H); 6.4(d,1H); 7.5(t,2H); 7.6(m,1H); 7.9 (d,2H).

Step C. Preparation of:

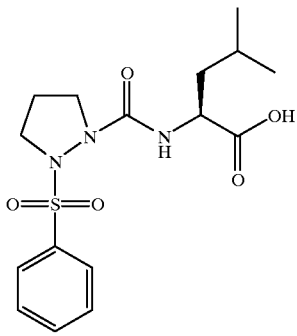

The product of Step B was submitted to the same reaction conditions outlined in Example 2 Step E to provide the desired product. FABMS: Calculated $M^+$=369.14; Obs $M^++H^+$=370.2. H-NMR (400 MHz, $CDCl_3$): 0.91(d,3H); 0.92(d,3H); 1.5(m,1H); 1.6(m,1H), 1.7(m,2H); 1.8–1.9(m, 1H); 2.4(m,1H); 3.4–3.5 (m,1H); 3.8(m,1H); 3.9(m,1H); 4.4(m,1H); 6.4(d,1H); 7.5(t,2H); 7.7(t,1H); 7.9(dd;2H).

EXAMPLE 4

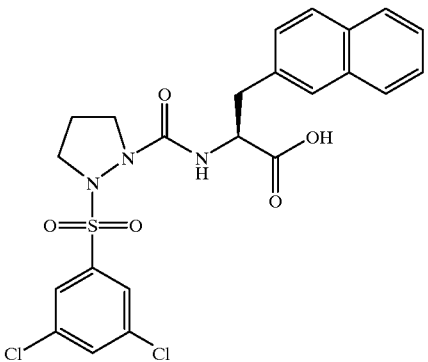

The experimental procedures described for the synthesis of the intermediates and final product of Examples 2 and 3 were repeated utilizing β-(2-naphthyl)-alanine tert-butyl ester and 3,5-dichlorophenylsulfonyl chloride to provide the desired product. FABMS: Calculated $M^+$=521.06; Obs $M^++H^+$=521.9, $M^++H^1+NH_3$=538.9. Characteristic $^1$H-NMR signals ($CDCl_3+CD_3OD$, 400 MHz): Spectrum very broad: 3.0–4.0 (broad multiplet); 7.35 (bs); 7.51 (bd); 7.6–7.8 (m).

EXAMPLES 5–7

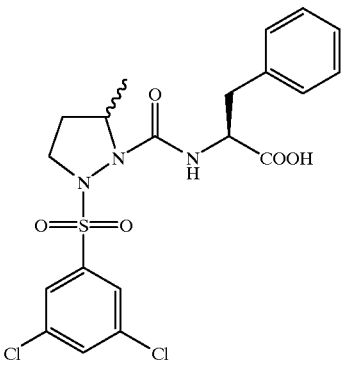

Example 5 and 6 seperated

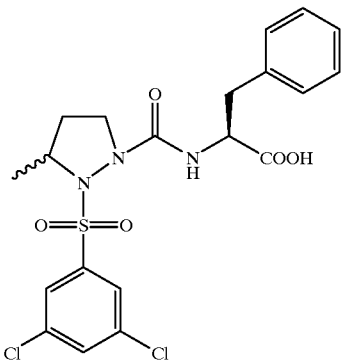

Example 7-mixture of isomers

Step A. Preparation of a mixture of 1-Boc-2-Cbz-5-methylpyrazolidine and 1-Boc-2-Cbz-3-methylpyrazolidine A suspension of 0.88 g (0.022 mol) of 60% sodium hydride in 20 mL of DMF was treated with a solution of 2.66 g (0.01 mol) of 1-Cbz-2-Boc-hydrazine in 10 mL of DMF at 0° C. The reaction mixture was stirred for 30 minutes at 0°

C. and 1 hour at room temperature. 1.3 mL (0.011 mol) of 1,3-dibromobutane was added neat and the mixture was stirred over night. The reaction mixture was diluted with 50 mL of water and extracted into ethyl acetate. The organic phase was washed with water 3 times followed by brine and was dried over MgSO$_4$. The mixture was filtered and concentrated in vacuo to give the desired product. $^1$H-NMR (CDCl$_3$400 MHz): 1.17 (d, 1.5H); 1.22 (d, 1.5 H:); 1.4 (s, 9H); 1.65 (m, 1H); 2.15 (m, 1H); 3.1–3.3 (m, 1H); 4.0 (m, 1H); 4.25 (m, 1H); 5.05–5.22 (m, 2H); 7.2–7.3 (m, 5H).

Step B. Preparation of 1-Cbz-3-methylpyrazolidine and 1-Cbz-5-methylpyrazolidine.

1.2 g (0.0037 mol) of the product of Step A was stirred in 8 mL of ethyl acetate saturated with hydrogen chloride for 2 hours. The solution was concentrated in vacuo. The residue was dissolved in CH$_2$Cl$_2$ and washed with 1 N NaOH solution. The organic phase was washed with brine and was dried over MgSO$_4$, filtered and concentrated in vacuo. The residue was purified by flash chromatography over silica gel eluting with 40% EtOAc/CH$_2$Cl$_2$ to give two products: less polar: 1-Cbz-3-methylpyrazolidine: H-NMR (CD$_3$CN, 500 MHz):1.08 (d, 3H); 1.58 (m, 1H); 2.15 (m, 1H); 3.15 (m, 1H); 3.45 (dd, 2H); 5.08(dd, 2H); 7.30–7.40 (m, 5H). more polar: 1-Cbz-5-methylpyrazolidine: H-NMR (CD$_3$CN, 500 MHz):1.20 (d, 3H); 1.59 (m, 1H); 2.24 (m, 1H); 2.70 m, 1H); 3.03 (m, 1H); 4.0 (m, 1H); 0.5.06 (s, 2H); 7.30–7.40 (m, 5H).

Step C-a.

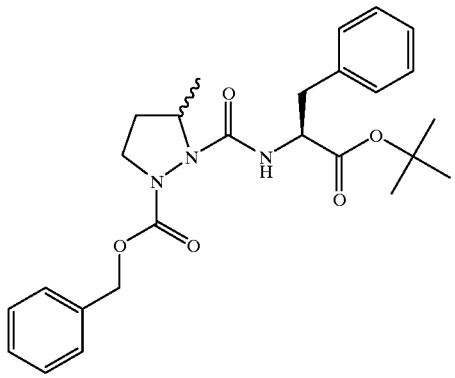

The method of Example 2, Step C was utilized using the less polar product of Step 2 above and tert-butyl (L)-phenylalanine as starting material. Purification by flash chromatography over silica gel eluting with 30% EtOAc/ hexanes gave the title product. H-NMR (CDCl$_3$, 400 MHz) :1.03 (d, 1.5H); 1.95 (d, 1.5H); 1.33 (s, 4.5H); 1.36 (s, 4.5H); 1.70 (m, 1H); 3.00 (m, 3H); 4.00 (m, 1H); 4.45 (m, 1H); 4.59 (m, 1H); 5.2 (m, 2H); 5.95 (t, 1H); 7.0–7.35 (m, 10H).

Step C-b.

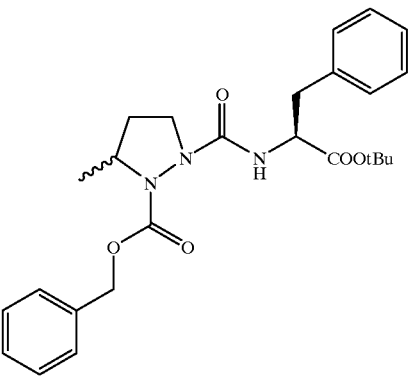

The method of Example 2 Step C was utilized using the more polar product of Step B above and tert-butyl (L)-phenylalanine as starting material. Purification by flash chromatography over silica gel eluting with 30% EtOAc/ hexanes gave the title product. H-NMR (CDCl$_3$400 MHz): 1.00 (d, 3H), 1.16 (d, 3H); 1.34, 1.38 (s, 9H); 1.60 (m, 2H); 2.12 (m, 1H); 3.05 (m, 4H); 4.25 (m, 2H); 4.6 (m, 1H); 5.15 (m, 2H); 5.95 (m, 1H); 7.1–7.35 (m, 10H).

Step D-a. Preparation of:

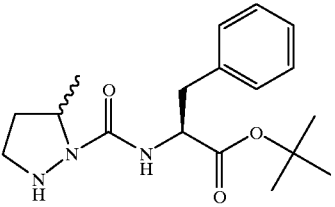

140 mg of the product of Step C-a was dissolved in 5 mL of MeOH and was hydrogenated under atmospheric pressure in the presence of 20 mg of 10% Pd/C overnight. The reaction mixture was filtered through celite and concentrated in vacuo to provide the title compound. $^1$H-NMR (CDCl$_3$ 400 MHz): 1.2–1.3 (m, 3H); 1.35 (d, 9H,; 1.55 (m, 1H); 2.28 (m, 1H); 2.55 (m, 0.5H); 3.1 (m, 2H); 4.15 (m, 1H); 4.60 (m, 1H); 6.60 (d, 0.5H); 6.75 (d, 0.5H); 7.1–7.3 (m, 5H).

Step D-b. Preparation of:

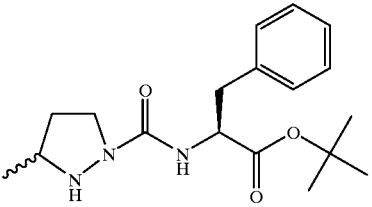

63 mg of the product of Step C-b was dissolved in 5 mL of MeOH and was hydrogenated under atmospheric pressure in the presence of 20 mg of 10% Pd/C overnight. The reaction mixture was filtered through celite and concentrated in vacuo to provide the title compound. $^1$H-NMR (CDCl$_3$): 1.12 (m, 3H); 1.36 (d, 9H); 1.60 (m, 2H); 2.18 (m, 1H); 3.5–3.6 (b, 2H); 4.6 (m, 1H); 6.70 (b, 1H); 7.1–7.3 (m, 5H).

Step E-a. Preparation of:

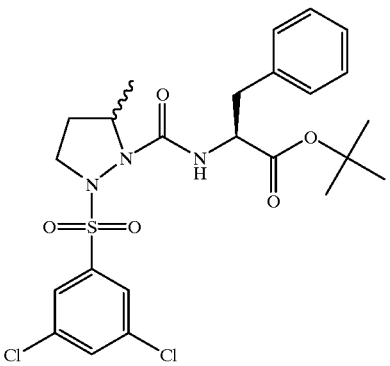

To a solution of 297 mg (0.87 mmol) of the product of Step D-a in 10 mL of CH$_2$Cl$_2$/THF was added 0.22 mg (1.74 mmol) of diisopropylethylamine and 20 mg of N,N-dimethylaminopyridine (DMAP). To the solution was added 260 mg (1.04 mmol) of 3,5-dichlorophenylsulfonyl chloride and the reaction was stirred for 5 hours at 50–60° C. Starting material was still evident by TLC. The reaction mixture was diluted with ethyl acetate and washed with water and dried over MgSO$_4$. The mixture was filtered and concentrated in vacuo. The residue was purified by preparative thin layer chromatography eluting with 30% EtOAc/hexanes to give 2 fractions. Structural assignment of the diastereomers was not made. less polar isomer: $^1$H-NMR (CDCl$_3$ 400 MHz): 0.95 (d, 3H); 1.42 (s, 9H); 2.05 (m, 1H); 3.00 (m, 1H); 3.10 (m, 2H); 4.00 (m, 1H); 4.10 (m, 1H); 4.55 (m, 1H); 6.65 (d, 1H); 7.1 (m, 2H); 7.2–7.3 (m, 3H); 7.6 (s, 1H); 7.,3 (d, 2H). more polar isomer:$^1$H-NMR (CDCl$_3$): 0.95 (d, 3H); 1.35 (s, 9H); 2.05 (m, 1H); 3.05 (m, 2H); 3.30 (m, 1H); 4.00 (m, 1H); 4.15 (m, 1H); 4.55 (m, 1H); 6.68 (d, 1H); 7.2–7.33(m, 5H); 7.6 (s, 1H); 7.78 (d, 2H).

step E-b. Preparation of:

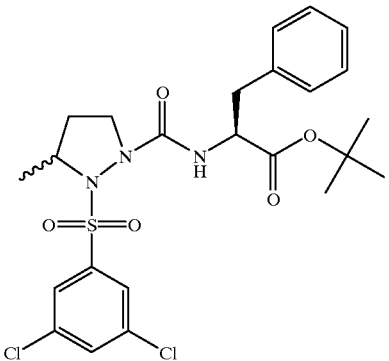

71 mg of the product of Step D-b was submitted to the same reaction conditions as described above for Step 4a except in a mixture of 1:1 CH$_2$Cl$_2$/THF. The reaction was stirred at room temperature for 1 hour and 50° C. for 4 hours followed by room temperature over night. Work up followed by preparative thin layer chromatography eluting with 25% EtOAc/hexanes gave the desired product as an inseparable mixture of diastereomers. $^1$H-NMR (CDCl$_3$ 400 MHz): 1.09 (d, 1.5H); 1.28(d, 1.5H); 1.38 (s, 5H); 1.42 (s, 4H); 1.70 (m, 1H); 1.8 (m, 1H); 2.3 (m: 1H); 3.0–3.2 (m, 2H); 4.05 (m, 2H); 4.58 (m, 1H); 6.65 (m, 1H); 7.1–7.3 (m, 6H); 7.6 (m, 1H); 7.78 (m, 2H).

Step F-a. Preparation of Example 5 and 6:

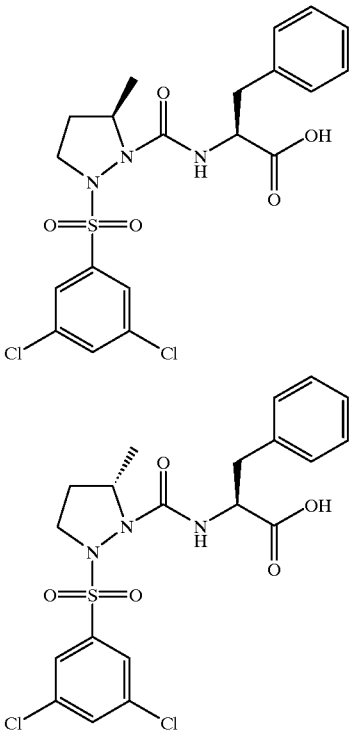

50 mg of the less polar product from Step E-a was dissolved in 1 mL of 50% CH$_2$Cl$_2$/TFA and was stirred at room temperature for 1 hour. The reaction mixture was concentrated in vacuo and the product was purified by preparative thin layer chromatography by eluting with 10% MeOH/CH$_2$Cl$_2$/0.5% HOAc to provide one of the two title products (less polar). The more polar isomer from Step 5a was committed to the same reaction and purification conditions to give the second diastereomer (more polar) derived from less polar isomer Step 5a: FABMS: Calculated M$^+$=485; Obs M$^+$+H$^1$+NH$_3$=503. $^1$H-NMR (CD$_3$OD): 0.92 (d, 3H); 1.15 (m, 1H); 2.07 (m, 1H); 3.08 (m, 2H); 3.25 (m, 1H); 4.00 (m, 2H); 4.4 (m, 1H); 7.1–7.3 (m, 5H); 7.88 (s, 1H); 7.92 (s, 2H). derived from more polar isomer Step 5a: FABMS: Calculated M$^+$=485; Obs M$^+$+H$^1$+NH$_3$=503. $^1$H-NMR (CD$_3$OD): 0.89 (d, 3H); 1.15 (m, 1H); 2.1 (m, 1H); 3.00 (m, 1H); 3.2 (m, 1H); 4.1 (m, 2H); 4.45 (b, 1H); 7.2–7.35 (m, 5H); 7.9 (s, 3H).

Step F-b. Preparation of Example 7

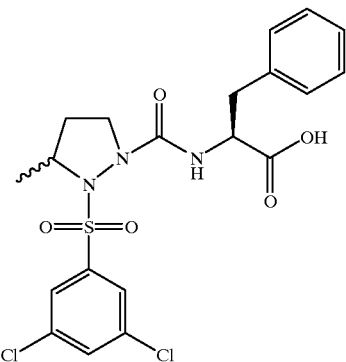

50 mg of the product of Step E-b was submitted to the same conditions described in the case of Step 6a. Purification by preparative thin layer chromatography eluting with 10% MeOH/CH$_2$Cl$_2$ gave the desired product as a mixture of diastereomers. FABMS: Calculated M$^+$=485; Obs M$^+$+H$^1$+NH$_3$=503. $^1$H-NMR (CD$_3$OD): 1.05 (d, 1.5H); 1.23 (d, 1.5H); 1.50 (m, 1H); 1.8–2.0 (b, 1H); 2.3 (m, 1H); 3.15 (b, 1H); 3.9 (m, 1H); 4.1 (m, 1H); 4.55 (b, 1H); 6.95 (b, 1H); 7.15–7.3 10 (m, 5H); 7.85 (m, 3H).

EXAMPLE 8

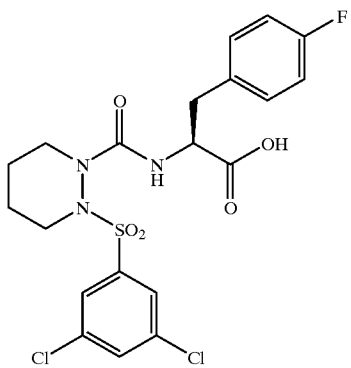

Step A. Preparation of 1-Boc-2-Cbz-hexahydropyridazine 1.5 g (37.5 mmol) of 60% sodium hydride in oil was suspended in 50 mL of DMF to which was added 5.0 g (18.7 mmol) of 1-Boc- 2-Cbz-hydrazine dissolved in 20 mL of dry DMF slowly over 30 minutes. The reaction mixture was stirred for 1 hour until H$_2$ evolution had ceased. To this mixture was added 2.24 mL (18.77 mmol) of 1,4-dibromobutane neat. The reaction mixture was stirred at room temperature over 3 days. The mixture was concentrated in vacuo and the residue was suspended in 150 mL of EtOAc. The mixture was washed with water twice, 5% citric acid twice, saturated aqueous NaHCO$_3$ solution, water and brine. The solution was dried over MgSO$_4$, filtered and concentrated in vacuo. The residue was purified by flash chromatography over silica gel eluting with 30% EtOAc/hexanes to give the desired product as a white solid. $^1$H-NMR (CDCl$_3$, 400 MHz):1.45 (bs, 9H); 1.62 (bm, 4H); 2.90 (bs, 2H); 4.15 (bm, 2H); 5.00–5.30 (m, 2H); 7.20–7.40 (bm, 5H).

Step B. Preparation of N-Boc-hexahydropyridazine

To a solution of 3.5 g of the product of Step A in 20 mL of MeOH was added 0.3 g of 10% Pd/C. The mixture was stirred under an atmosphere of hydrogen gas overnight. The suspension was filtered through celite and concentrated in vacuo to give the product as a white solid. $^1$H-NMR ((CDCl$_3$, 400 MHz):1.21 (s, 9H); 1.50–1.80 (m, 4H); 2.91 (dd, 2H); 3.53 (dd, 2H).

Step C. Preparation of hexahydropyridazine

The product of Step B was dissolved in ethyl acetate and treated with a solution of hydrogen chloride dissolved in ethyl acetate. A white precipitate formed immediately and was recovered by filtration after 20 minutes and was washed with ethyl acetate to give the desired product. This material may be the mono or dihydrochloride or a mixture of both. $^1$H-NMR (CD$_3$OD): 1.8 (m, 4H); 3.14 (m, 4H).

Step D. Preparation of:

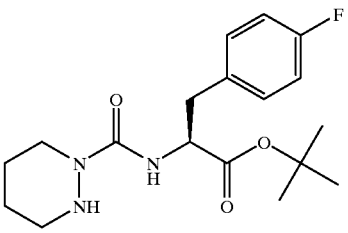

To a solution of 0.1 g (0.42 mmol) 4-fluorophenylalanine tert-butyl ester in 1.0 mL of CH$_2$Cl$_2$ at 0° C. was added 0.065 g (0.5 mmol) of diisopropyl ethyl amine followed by 0.093 g (0.46 mmol) of p-nitrophenyl chloroformate as a solid. After 30 minutes a solution of 82.7 mg (0.52 mmol) of pyridazine dihydrochloride (Step C) and 0.2 g (1.56 mmol) of diisopropylethylamine in 1.5 mL of CH$_2$Cl$_2$ was added. The reaction mixture was stirred for 2.5 hours and diluted with 20 mL of ethyl acetate. The solution was washed with water twice followed by brine and was dried over MgSO$_4$. The mixture was filtered and concentrated in vacuo. The residue was purified by flash silica gel chromatography eluting with 45% EtOAc/hexanes to provide the title compound. $^1$H-NMR (CDCl$_3$, 400 MHz): 1.38 (s, 9H); 1.60 (b, 6H); 2.8 (b, 2H); 3.05 (m, 2H); 15 4.57 (m, 1H); 6.75 (b, 1H); 6.95 (m, 2H); 7.15 (m, 2H).

Step E. Preparation of

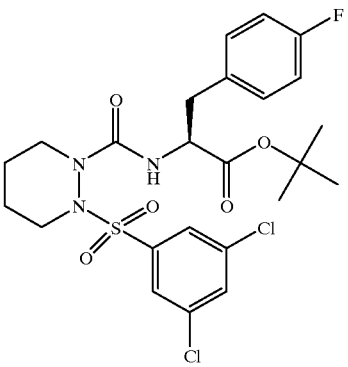

A solution of 0.05 g (0.14 mmol) of the product of Step D in 1.0 mL of CH$_2$Cl$_2$ was treated with 10 mg of DMAP and 36.6 mg (0.28 mmol) of diisopropylethylamine and 3,5-dichlorophenylsulfonyl chloride. The reaction mixture was stirred at room temperature over night and diluted with 10 mL of ethyl acetate. The solution was washed with water twice followed by brine and was dried over MgSO$_4$. The mixture was filtered and concentrated in vacuo. The residue was purified by preparative thin layer chromatography eluting with 35% EtOAc/hexanes to provide the title compound.

¹H-NMR (CDCl₃ 400 MHz): 1.35 (s, 4.5H); 1.40 (s, 4.5H); 1.50 (b, 4H); 2.7 (m, 1H); 2.9 (m, 2H); 3.15 (m, 1H); 4.15 (m, 2H); 4.45 (m, 1H); 5.95 (d, 0.5H); 6.1 (d, 0.5H); 6.9–7.15 (m, 4H); 7.53 (m, 1H); 7.78 (m, 2H).

Step F. Preparation of:

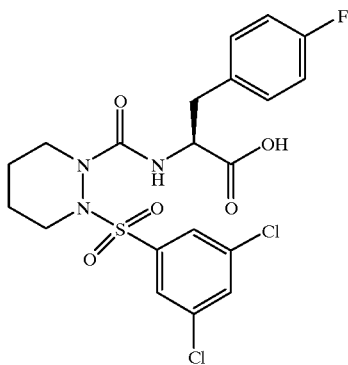

11.0 mg of the product of Step E was stirred for 3 hours in 1 mL of 50% TFA/CH₂Cl₂. The reaction mixture was concentrated in vacuo and purified by preparative thin layer chromatography over silica gel eluting with 10% MeOH/CH₂Cl₂ to give the title product. FABMS: Calculated M⁺=504; Obs M⁺+H⁺=505, M⁺+H¹+NH₃=522. ¹H-NMR (CD₃OD 400 MHz):1.6 (b, 4H); 2.78–3.3 (b, 4H); 4.1 (m, 2H); 4.4 (b, 1H); 6.6 (b, 1H); 7.00 (m, 2H); 7.15 (m, 2H); 7.75 (d, 1H); 7.85 (d, 2H).

EXAMPLE 9

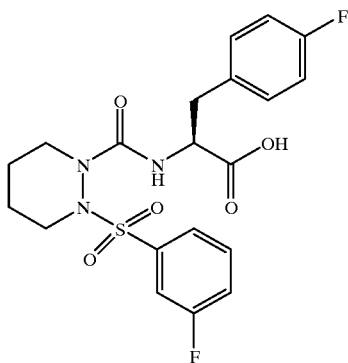

The experimental procedures-described in the case of Example 8 were utilized substituting 3-fluorophenylsulfonyl chloride in place of 3,5 dichlorophenylsulfonyl chloride. The title compound was isolated following preparative thin layer chromatography over silica gel eluting with 10% MeOH/CH₂Cl₂ to give the title product. FABMS: Calculated M⁺=453; Obs M⁺+H⁺=454, M⁺+H¹+NH₃=471. ¹H NMR (CD₃OD, 400 MHz): 1.3–1.7 (m, 4H); 2.6–3.00 (m, 2H); 3.05 (m, 1Hi); 3.25 (m, 1H); 4.0–4.2 (m, 2H); 4.3 (m, 1H); 7.6–7.8 (m, 3H).

SOLID PHASE SYNTHESIS OF EXAMPLES 10–19.

Step A. Synthesis of N-Boc-pyrazolidine.

10.7 g (33 mmol) of the product of Example 2 Step B was dissolved in 40 mL of MeOH. 1.0 g of 10% Pd/C was added and the reaction mixture was stirred under an atmosphere of hydrogen over 24 hours. The mixture was filtered through celite and concentrated in vacuo to give the desired product. H-NMR (400 MHz, CDCl₃): 1.5(s,9H); 2.0(m,2H); 3.0(t, 2H); 3.4(t,2H).

Step B. Synthesis of 1-Boc-2-FMOC-pyrazolidine.

6.0 g (35 mmol) N-Boc-pyrazolidine was dissolved in 20 mL of methylene chloride to which was added 7.2 mL (42 mmol) of diisopropylethyl amine at 0° C. To this solution was added portionwise 9.0 g of 2-fluorenylmethylchloroformate. The solution was stirred at room temperature for 3 hours. The reaction mixture was washed with 5% citric acid, water and brine. The organic phase was dried over MgSO₄, filtered and concentrated in vacuo to give the product as a white solid. H-NMR (400 MHz, CDCl₃): 2.3(m,2H); 3.5(t,2H); 3.7(t,2H); 4.2(t,1H); 4.4(d,2H); 7.3(d,2H); 7.4(t,2H); 7.5(d,2H); 7.7(d,2H).

Step C. Synthesis of N-FMOC-pyrazolidine.

7.4 grams of N-Boc-N-FMOC-pyrazolidine was dissolved in 20 mL of 50% trifluoroacetic acid in methylene chloride for 1 hour. The reaction mixture was concentrated in vacuo. The residue was dissolved in toluene and concentrated in vacuo to dryness to give a white solid. H-NMR (400 MHz, CDCl₃): 2.3(m,2H); 3.5(t,2H); 3.7(t,2H); 4.2(t,1H); 4.4(d,2H); 7.3(d,2H); 7.4(t,2H); 7.5(d,2H); 7.7(d,2H).

Step D. General procedure for the solid phase synthesis of azapeptides.

0.2 g (0.04 mmol, based on approximate loading of amino acid on resin of 0.2 mmol/g) of Tantagel-HMPB-amino acid resin:

Tantagel-HMPB-amino acid resin

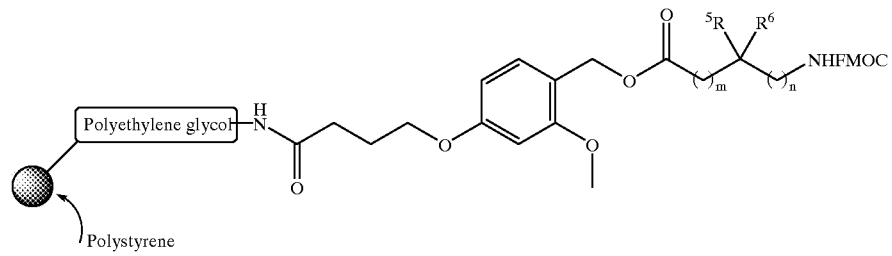

was suspended in 1.5 mL of a freshly prepared solution of 20% piperidine in DMF for 20 minutes. Treatment with 20% piperidine/DMF was repeated twice. The resin was washed with DMF 3 times, $CH_2Cl_2$ two times, MeOH, $CH_2Cl_2$ twice. A solution of 0.25 g of N-FMOC-pyrazolidine (0.8 mmol) in 1.5 mL of 50% $CH_2Cl_2$/THF at 0° C. was treated with 0.35 mL (2.0 mmol) of diisopropylethylamine followed by 0.06 g (0.19 mmol) of triphosgene in 0.5 mL of $CH_2Cl_2$. The solution was stirred for 30 minutes and then added to the previously prepared resin (note: for more than one reaction at a time the cocktail of activated N-FMOC-pyrazolidine was multiplied by the appropriate factor). The resin was mixed for 1 hour with the activated pyrazolidine and then filtered. The resin was washed with 50% $CH_2Cl_2$/THF 3 times. A small amount of resin was removed (1 mg) and submitted to the Kaiser test to insure that the free amino groups had been successfully acylated. The resin was treated with 20% piperidine/DMF three times followed by washing with DMF 3 times and $CH_2Cl_2$ twice. To the resin was added a solution of 27 mg (0.14 mmol) 4-fluorophenylsulfonyl chloride (a molar equivalent amount of 3,5 dichlorophenyl sulfonyl chloride was used in the case of Example 5) in 1 mL of methylene chloride, 0.04 mL (0.22 mmol) of diisopropylethyl amine and a catalytic amount (approximately 5 mg) of dimethylamino pyridine. The resin was mixed with the sulfonyl chloride over night. The reaction mixture was drained and a fresh solution of the sulfonylation reagents were added and the resin was mixed over night. The resin was filtered and washed: $CH_2Cl_2$ 3 times, DMF 3 times, $CH_2Cl_2$ 2 times, MeOH, $CH_2Cl_2$, MeOH, $CH_2Cl_2$ 2 times. The resin was treated with 1.5 mL of a 10% solution of trifluoroacetic acid in methylene chloride 3 times with the filtrate collected after each treatment. The combined filtrates were concentrated in vacuo and azeotroped from toluene to provide the desired products. Lyophilization from 50% acetonitrile/water was also used to provide the products as amorphous solids. The products were analyzed by HPLC and mass spectroscopy.

The following compounds were prepared by the procedure indicated above:

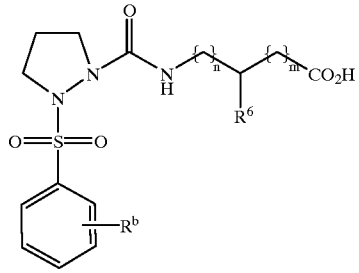

| EXAMPLE # | n/m | $R^b$ | $R^6$ | Observed FAB MS ($M^+ + 1$) |
|---|---|---|---|---|
| 10 | 0/0 | 3,5-dichloro | (S)-phenylmethyl | 472.3 |
| 11 | 0/0 | 4-fluoro | (S)-n-butyl | 388.4 |
| 12 | 0/0 | 4-fluoro | phenyl | 408.6 |
| 13 | 0/0 | 4-fluoro | (S)-4'-biphenylmethyl | 498.5 |
| 14 | 0/1 | 4-fluoro | methyl | 360.2 |
| 15 | 0/1 | 4-fluoro | phenylmethyl | 422.3 |
| 16 | 0/1 | 4-fluoro | 2-methylpropyl | 402.3 |
| 17 | 0/1 | 4-fluoro | phenyl | 422.3 |

-continued

| EXAMPLE # | n/m | $R^b$ | $R^6$ | Observed FAB MS ($M^+ + 1$) |
|---|---|---|---|---|
| 18 | 1/0 | 4-fluoro | methyl | 360.2 |
| 19 | 0/0 | 4-fluoro | (S)-phenylmethyl | 422.3 |

Alternative Solid Phase Synthesis of Compound of Example 19.

Step A. Synthesis of pyrazolidine hydrochloride.

0.74 g of N-Boc pyrazolidine was dissolved in ethyl acetate to which was added an excess of a saturated solution of hydrogen chloride in ethyl acetate. The mixture was stirred for one hour and filtered. The resulting white solid was washed with ethyl acetate and dried in vacuo to give the desired product as a hygroscopic white solid, which may be the dihydrochloride, monohydrochloride or mixture of both. $^1$H-NMR ($CD_3OD$): 1.95 (m, 2H, 3.04 (t, 4H).

Step B.

0.1 g (0.02 mmol) of resin was prepared for acylation by treatment with 20% piperidine/DMF as described above. To the resin was added a solution of 0.1 g (0.5 mmol) of p-nitrophenyl chloroformate, 0.064 g (0.65 mmol) diisopropylethyl amine in 1.0 mL of 50% $CH_2Cl_2$/THF. The mixture was agitated for 40 minutes. The resin was filtered and washed twice with $CH_2Cl_2$/THF. A solution of 0.072 g (0.5 mmol) and 0.19 g (1.5 mmol) diisopropylethyl amine in 2 mL of 50% $CH_2Cl_2$/THF was added and the mixture was agitated for 1 hour, filtered and washed 3 times with 50% $CH_2Cl_2$/THF. The resin was treated with 0.097 g (0.5 mmol) of 4-fluorophenylsulfonyl chloride and 0.129 g (1.0 mmol) of diisopropylethyl amine in 50% $CH_2Cl_2$/THF over 48 hours. Washing of the resin as described above, followed by TFA treatment and concentration provided the product of Example 19.

EXAMPLE 20

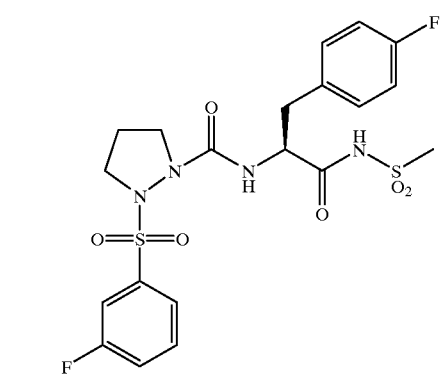

Step A. Preparation of:

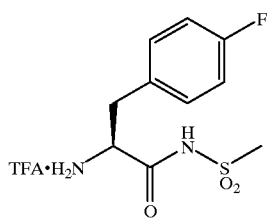

To a solution of 1.0 g (3.5 mmol) of N-Boc-4-fluoro-L-phenylalanine in 10 mL of methylene chloride and 2 mL of DMF was added 0.47 g (5 mmol) of methylsulfonamide, 0.61 g (5 mmol) of 4-DMAP and 0.95 g (5 mmol) 1-(3-dimethylaminopropyl)-3-ethylcarbodiimide HCl (EDC). The reaction mixture was stirred over night at room temperature, diluted with ethyl acetate and washed with 1N HCl three times, followed by brine. The organic phase was dried over $MgSO_4$, filtered and concentrated in vacuo to provide the N-Boc acyl sulfonamide. H-NMR (300 MHz, CDCl3): 1.4 (s,9H); 2.9 and 3.15 (pair of dd, 2H), 3.25 (s, 3H), 4.45 (bs, 1H); 5.32 (bd, 1H); 6.95 (t, 2H), 7.15 (m, 2H); 9.85 (bs, 1H). The material was dissolved in 20 mL of methylene chloride and 20 mL of TFA and was stirred for 3 hours. The reaction mixture was concentrated in vacuo, redissolved in toluene and concentrated to give a glass.

Step B. Preparation of:

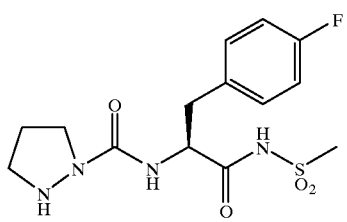

To a solution of 0.15 g (0.4 mmol) of the product of Step A and 0.13 g (1 mmol) of diisopropyl ethyl amine in 2.5 mL of methylene chloride at 0° C. was added 88 mg (0.44 mmol) p-nitrophenyl chloroformate. After 30 minutes a solution of 69 mg (0.5 mmol) of pyrazolidine dihydrochloride and 0.18g (1.44 mol) in 1 mL of methylene chloride was added. The reaction mixture was stirred allowing the temperature to increase to room temperature over night. The mixture was diluted with ethyl acetate and washed with 5% citric acid, water and brine. The organic phase was dried over $MgSO_4$, filtered and concentrated in vacuo. The residue was purified by chromatograhy over LH20 eluting with methanol to give the desired product as a colorless gum. FABMS: Calculated $M^+=358$; Obs $M^++H^1=359$. $^1$H-NMR (CDCl$_3$): 1.98 (m, 2H); 2.61 (m, 1H); 2.8–3.0 (m, 4H), 3.23 (s, 3H), 3.50 (m, 2H); 5.45 (m, 1H); 6.98 (t, 2H), 7.15 (m, 2H); 9.42 (s, 1H).

Step C. Preparation of

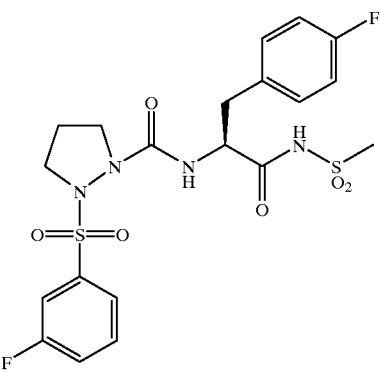

0.09 g (0.25 mmol) of the product of Step B was combined with 34 mg (0.26 mmol) of diisopropyl ethyl amine and 53 mg ol 3-fluorophenylsulfonyl chloride and 5 mg of DMAP in 1.5 mL of methylene chloride. The reaction mixture was stirred over night, diluted with ethyl acetate and was washed with 5% citric acid, water and brine. The organic phase was dried over $MgSO_4$, filtered and concentrated in vacuo. The residue was purified by prep-TLC over silica gel eluting with 2% MeOH/CH$_2$Cl$_2$ to give the desired product. FABMS: Calculated $M^+=516$; Obs $M^++H^1=517$. NMR is complex due to the presence of rotomers.

EXAMPLE 21

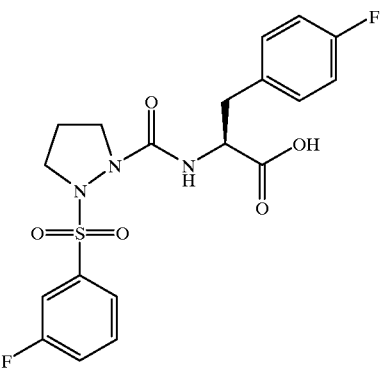

The procedure described in Example 9 was followed, utilizing pyrazolidine dihydrochloride as the hydrazine. The product was purified by prep-TLC over silica gel eluting with 10% chloroform/CH$_2$Cl$_2$ 0.1% acetic acid to give the product as a glass. FABMS: Calculated $M^+=439$; Obs $M^++H^1=440$. $^1$H-NMR (400 MHz, CD$_3$OD): Mixture of rotomers characteristic signals: 1.5–1.9 (m, 2H); 2.40 (m, 1H); 3.0–3.29 (m, 2H); 3.42 (m); 1.70–1.90 (m, 2H); 4.20–4.40 (m, 1H); 7.0 (t, 2H); 7.17 (dd, 1H); 7.35 (m, 1H); 7.50–7.80 (m, 4H).

EXAMPLE 22

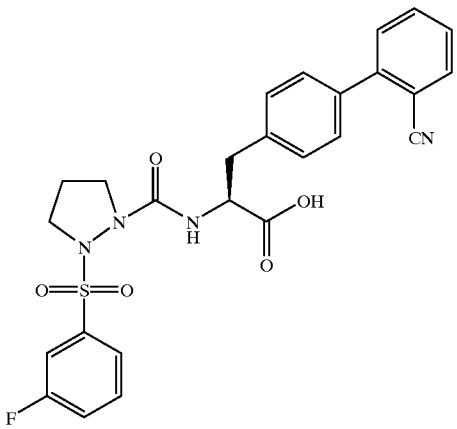

Step A. Preparation of:

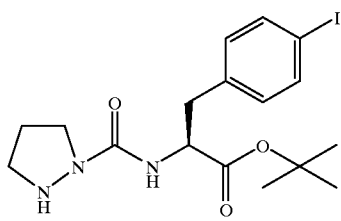

0.87 g (2.75 mmol) of the tert-butyl ester of 4-iodophenylalanine and 0.45 g (3.1 mmol) of pyrazolidine dihydrochloride were submitted to the reaction conditions described in the case of Example 20, Step B. The crude product was purified by Biotage flesh chromatography over silica eluting with 50% EtOAc/hexanes to provide the product as a glass. $^1$H-NMR (400 MHz, CDCl$_3$): 1.40 (s, 9H); 2.0 (m, 2H); 2.82 (bs, 2H); 3.0 (AB, 2H); 3.46 (bs, 2H); 4.60 (q, 1H); 6.70 (d, 1H); 6.92 (d, 2H); 7.59 (d, 2H).

Step B. Preparation of:

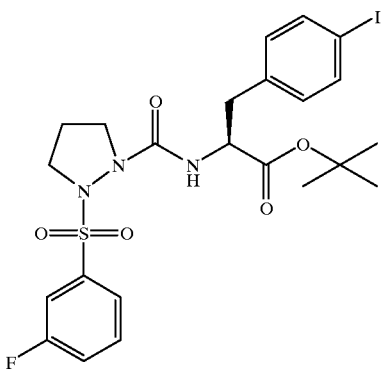

0.45 g (1.02 mmol) of the product of Step A was acylated with 0.24 g (1.22 mmol) of 3-fluorophenylsulfonyl chloride in the presence o 1.22 mmol of diisopropyl ethyl amine and a catalytic amount ol DMAP as described in Example 20 Step 3. The product was isolated by Biotage flash chromatography over silica gel eluting with 50% CHCl$_3$/CH$_2$Cl$_2$ to give the product as a glass. 1H-NMR (400 MHz, CDCl$_3$): mixture of 2 rotomers. Characteristic signals: 1.39 and 1.41 (s); 1.55–1.90 (m:); 2.35 (m); 2.9–3.1 (m); 3.22 (m); 3.42 (m); 3.75 (m); 3.95 (m); 4.50 (m); 4.60 (m); 6.65 (d); 6.90 (d); 7.10 (d); 7.39 (m); 7.50–7.75 (m).

Step C. Preparation of

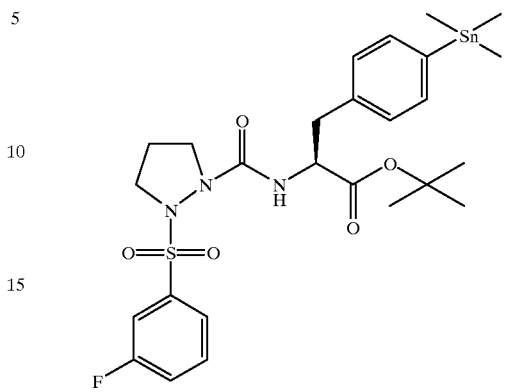

0.06 g (0.1 mmol) of the product of Step B, 1 mg of lithium chloride, 1 mg of triphenylphosphine were combined and dissolved in 1 mL of dry dioxane. 0.045 g (0.14 mmol) of hexamethyldistannane and 6 mg of tetrakistriphenylphosphine was added and the reaction was degassed under nitrogen. The mixture was heated at 80° C. for 90 minutes at which time a black suspension was evident. The reaction mixture was diluted with water (5 mL) and extracted with ethyl acetate. The organic phase was washed with brine and dried over MgSO$_4$, filtered and concentrated in vacuo. The residue was purified by preparatory thin layer chromatography eluting with 50% EtOAc/hexanes to provide the desired product as an oil. 1H-NMR (300 MHz, CDCl$_3$): mixture of rotomers: Characteristic signals : 0.39 (two singlets, 9H); 1.35 and 1.45 two singlets, 9H); 1.5–1.9 (m, 2H); 2.36 (bq, 1H), 2.9–3.25 (m), 3.40 (m); 3.75 (m, 1H), 3.95 (m,1H); 4.52 (m, 1H); 6.62(m, 1H); 7.09 ((d, 1H); 7.25–7.55 (m); 7.62 (d, 1H); 7.72 (d, 1H).

Step D. Preparation of

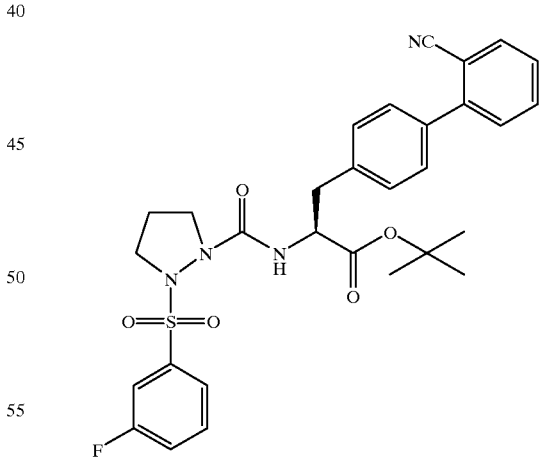

To a solution of 39 mg (0.061 mmol) of the product of Step C in 1 mL of toluene was added 21 mg (0.09 mmol) of 2-iodobenzonitrile and 5 mg of bistriphenylphosphine palladium dichloride. The reaction mixture was degassed under nitrogen and heated at 100° C. for 12 hours. The reaction mixture was concentrated in vacuo and the residue was preparatory thin layer chromatography eluting with 50% EtOAc/hexanes to provide the product as a glass. $^1$H-NMR (300 MHz, CDCl$_3$): mixture of rotomers, very broad spectrum: Characteristic signals :1.40 and 1.51 (s); 1.80 (bm); 2.40 (bm); 3.0–2.5 (mn); 3.75 (bm); 3.95 (bm); 4.62 (bm); 6.70 (d); 7.25–7.80 (bm). FABMS: Calculated M⁺=578; Obs M⁺+H¹=579

Step E. Preparation of

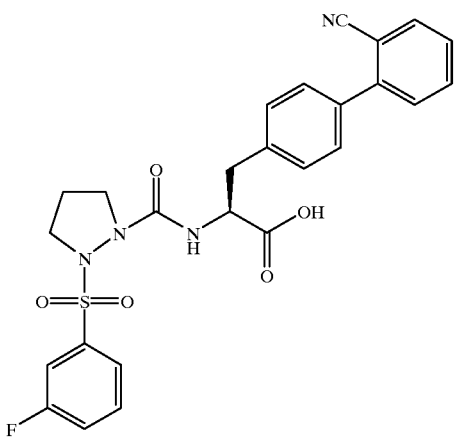

The product of Step E was stirred in 1 mL of 50% TFA/CH₂Cl₂ for 2 hours. The reaction mixture was concentrated in vacuo and the residue was purified by preparatory thin layer chromatography eluting with 7% MeOH/CH₂Cl₂ 1% HOAc to provide the product as a glass. FABMS: Calculated M⁺=522; Obs M⁺+H¹=523, M⁺+18=540

EXAMPLE 23

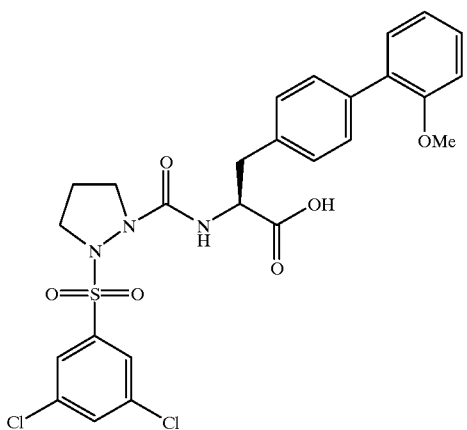

Step A. N-(Boc)-(S)-4-iodo-phenylalanine tert-butyl ester

To a suspension of 7.5 g (0.019 m) of 4-iodophenylalanine tert-butyl ester in 100 mL of dichloromethane was added 2.52 g 0.019 m of diisopropyl ethyl amine followed by 4.14 g of di-tert-butyl-dicarbonate. The reaction mixture was stirred over night at room temperature, washed with 1N HCl (2×25 mL), water (2×25 mL), saturated NaHCO₃ (1×25 mL), brine (1×25 mL) and was dried over MgSO₄. The mixture was filtered and concentrated in vacuo to give the desired product as a gum 8.8 g (100% yield). 300 MHz ¹H NMR (CDCl₃): 1.39 (s, 18H); 2.98 (AB, 2H); 4.4 (dd, 2H); 5.0 bd, 1H); 6.92 (d, 2H); 7.62 (d, 2H).

Step B. N-(Boc)-(S)-2'-methoxy-biphenylalanine, tert-butyl ester.

7.97 g (0.018 m) of the product of Step A was dissolved in 160 mL of 2:1 toluene:ethanol. To this solution was added 2.99 g (0.0198 m) 2-methoxyphenylboronic acid, 0.69 g of tetrakistriphenylphosphine palladium (O) and 22.7 mL (0.45 m) of 2.0 M sodium carbonate in water. The reaction mixture was degassed three times and then heated at 90° O for 90 minutes at which time the reaction mixture was black. The mixture was diluted with 300 mL of ethyl acetate and was washed with water (3×150 mL) and brine (2×100 mL) and was dried over MgSO₄. The mixture was filtered and concentrated in vacuo. The residue was purified by flash chromatography over silica gel eluting with 10% EtOAc/hexanes to give 6.89 g (88% yield) of the desired product as a white solid. 300 MHz ¹H NMR (CDCl₃): 1.45 (s, 18H); 3.10 (d, 2H); 3.80 (s, 3H); 4.5 (dd, 2H); 5.1 bd, 1H); 7.0 (m, 2H); 7.22 (d, 2H); 7.30 (d, 2H); 7.49 (d, 2H); 7.62 (d, 2H).

Step C. Preparation of (S)-2'-methoxy-biphenylalanine, tert-butyl ester, hydrochloride.

To a solution of 4.85 g (0.0113 m) of the product of Step B in 100 mL of tert-butyl acetate was added 5.53 g (0.056 m) of concentrated sulfuric acid. The solution was stirred at room temperature for 2 hours and then carefully neutralized by addition of saturated aqueous NaHCO₃ solution. The solution was washed with NaHCO₃ solution, dried over NaSO₄, filtered and concentrated in vacuo. The residue was dissolved in 50 mL of ether and treated with anhydrous HCl gas with stirring to give a white precipitate. The solid was collected by filtration, washed with ether and dried in vacuo to give the desired product. 300 MHz ¹H NMR (CD₃OD): 1.45 (s, 9H); 3.20 (d, 2H); 3.79 (s, 3H); 4.21 (t, 1H); 7.03 (m, 2H); 7.28 (m, 2H); 7.31 (d, 2H); 7.50 (d, 2H).

Step D. Preparation of

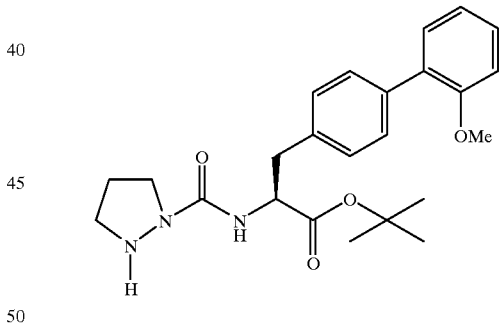

0.15 g (0.4 mmol) of the product of Step C was submitted to the reaction conditions described for Example 20, Step B. The product was purified by MPLC Lobar B silica column eluting with 50–70% EtOAc/hexanes to give 82 mg of the product. 300 MHz ¹H NMR (CDCl₃): Two conformers present characteristic signals: 1.42 and 1.46 (s, 9H total); 2.0 (m, 2H); 2.82 (bm, 2H); 3.12 (d, 2H); 3.50 (t, 1H); 3.79 (s, 3H); 4.65 (dd, 1H); 6.80 (d, 1H); 7.0 (m, 2H); 7.20–7.35 (m, 3H); 7.42 (d, 2H); 7.55 (dd, 1H).

Step E. Preparation of

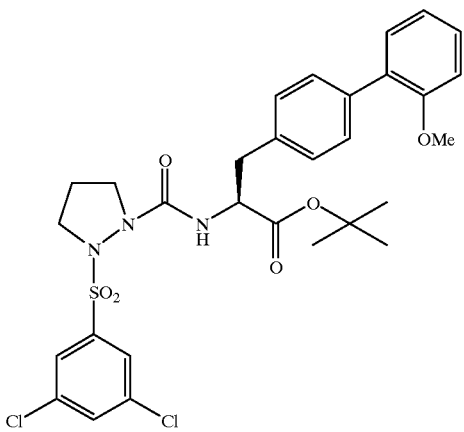

To a solution of 0.077g (0.18 mmol) of the product of Step D in 1 mL of $CH_2Cl_2$ was added 0.015 g of pyridine followed by 0.046 g (0.19 mmol) of 3,5-dichlorophenylsulfonyl chloride. The solution was stirred at room temperature over night. The reaction mixture was concentrated in vacuo and purified by preparatory thin layer chromatography over silica gel eluting with 50% EtOAc/hexanes to give 0.028 g of the desired product. 300 MHz $^1$H NMR ($CDCl_3$): Two conformers present characteristic signals: 1.39 and 1.49 (s, 9H total); 2.51 (m, 1H); 3.0–3.25 (m); 3.45 (m); 3.72 (m); 3.81 (s, 3H); 4/03 (m); 4/60 (m, 1H); 6.60 (t, 1H); 7.00 (m, 2H); 7.15 (d, 1H); 7.31 (m, 2H); 7.49 (m, 2H); 7.61 (m, 1H); 7.80 (m, 2H).

Step F. Preparation of

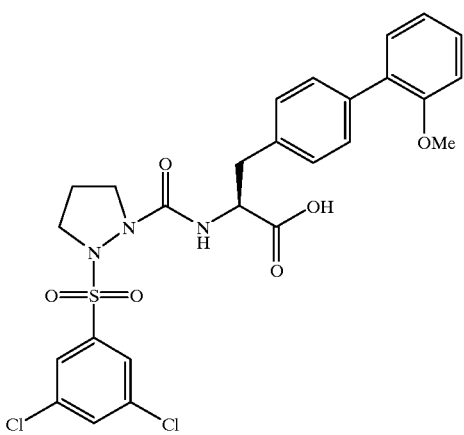

The product of Step E was stirred with 1.5 mL of 50% $TFA/CH_2Cl_2$ for 1 hour. The reaction mixture was concentrated in vacuo and the residue was purified by preparatory thin layer chromatography over silica gel eluting with 5% $MeOH/CH_2Cl_2$ 1% HOAc. to give the desired product. FABMS: Calc. $C_{26}H_{35}N_3Cl_2SO_6$; 577; Obs.: 578

EXAMPLE 24

Inhibition of VLA-4 Dependent Adhesion to BSA-CS-1 Conjugate

Step A. Preparation of CS-1 Coated Plates.

Untreated 96 well polystyrene flat bottom plates were coated with bovine serum albumin (BSA; 20 μg/mL) for 2 hours at room temperature and washed twice with phosphate buffered saline (PBS). The albumin coating was next derivatized with 10 μg/mL 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 μg/mL and allowed to react for 2 hours at room temperature. The plates were washed twice with PBS and stored at 4° C.

Step B. Preparation of Fluorescently Labeled Jurkat Cells.

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/mL penicillin, 50 μg/mL streptomycin and 2 mM glutamine. Fluorescence activated cell sorter analysis with specific monoclonal antibodies confirmed that the cells expressed both the α4 and β1 chains of VLA-4. The cells were centrifuged at 400× G for five minutes and washed twice with PBS. The cells were incubated at a concentration of $2 \times 10^6$ cells/mL in PBS containing a 1 KM concentration of a fluorogenic esterase substrate (2', 7'-bis-(2-carboxyethyl)-5-(and -6)-carboxyfluorescein, acetoxymethyl ester; BCECF-AM; Molecular Probes Inc., Eugene, Oreg.; catalog #B-1150) for 30–60 minutes at 37° C. in a 5% $CO_2$/air incubator. The fluorescently labeled Jurkat cells were washed two times in PBS and resuspended in RPMI containing 0.25% BSA at a final concentration of $2.0 \times 10^6$ cells/mL.

Step C. Assay Procedure.

Compounds of this invention were prepared in DMSO at 100× the desired final assay concentration. Final concentrations were selected from a range between 0.001 nM-100 μM. Three μL of diluted compound, or vehicle alone, were premixed with 300 μL of cell suspension in 96-well polystyrene plates with round bottom wells. 100 μL aliquots of the cell /compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 25

Antagonism of VLA-4 Dependent Binding to VCAM-Ig Fusion Protein.

Step A. Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3';

5'-PCR primer:

5'-ATAGGAATTCCAGCTGCCACCATGCCTGGGAAG-ATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:
MPGKMVVILGASNILWIMFAASQAFKI-ETTPESRYLAQIGDSVSLTC STTGCESPFFSWRTQID-SPLNGKVTNEGTTSTLTMNPVSFGNEHSYLC TATCESRKLEKGIQVEIYSFPKDPEIHLSGPLEAGKPIT-VKCSSVADVY PFDRLEIDLLKGDHLMKSQE-FLEDADRKSLETKSLEVTFTPVIEDIGKV LVCRAKL-HIDEMDSVPTVRQAVKEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCA24 fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-KI (ATCC CCL 61) cells using calcium-phosphate DNA precipitation (Specialty Media, Lavalette, N.J.). Stable VCAM-Ig producing clones were selected according to standard protocols using 0.2–0.8 mg/mL active G418 (Gibco, Grand Island, N.Y.), expanded, and cell supernatants were screened for their ability to mediate Jurkat adhesion to wells previously coated with 1.5 $\mu$g/mL (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B. Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using UV and radiometric detection.

Step C. VCAM-Ig Binding Assay.

Compounds of this invention were prepared in DMSO at 100× the desired final assay concentration. Final concentrations; were selected from a range between 0.001 nM-100 $\mu$M. Jurkat cells were centrifuged at 400× G for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with MnCl$_2$ at a final concentration of 1 mM. Compounds were assayed in Millipore MHVB multiscreen plates (cat# MHVBN4550, Millipore Corp., Mass.) by making the following additions to duplicate wells: (i) 200 $\mu$L of binding buffer containing 1 mM MnCl$_2$; (ii) 20 $\mu$l of $^{125}$I-VCAM-Ig in binding buffer containing 1 mM MnCl$_2$ (final assay concentration~100 pM); (iii) 2.5 $\mu$L of compound solution or DMSO; (iv) and 0.5×10$^6$ cells in a volume of 30 $\mu$L. The plates were incubated at room temperature for 30 minutes, filtered on a vacuum box, and washed on the same apparatus by the addition of 100 AL of binding buffer containing 1 mM MnCl$_2$. After insertion of the multiscreen plates into adapter plates (Packard, Meriden, Conn., cat# 6005178), 100 $\mu$L of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the IC$_{50}$ was determined from a ten point titration using a validated four parameter fit algorithm.

EXAMPLE 26

Antagonism of $\alpha_4\beta_7$ Dependent Binding to VCAM-Ig Fusion Protein.

Step A. $\alpha_4\beta_7$ Cell line.

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/100 $\mu$g streptomycin/2 mM L-glutamine at 37° C., 5% carbon dioxide. The cells were pelleted it 1000 rpm for 5 minutes and then washed twice and resuspended in binding buffer (25 mM HEPES, 150 mM NaCl, 0.1% BSA, 3 mM KCl, 2 mM Glucose, pH 7.4).

Step B. VCAM-Ig Binding Assay.

Compounds of this invention were prepared in DMSO at 100× the desired final assay concentration. Final concentrations were selected from a range between 0.001 nM-100 $\mu$M. Compounds were assayed in Millipore MHVB multiscreen plates (Cat# MHVBN45150) by making the following sequential additions to duplicate wells: (i) 100 $\mu$L/well of binding buffer containing 1.5 mM MnCl$_2$; (ii) 10 $\mu$l/well $^{125}$I-VCAM-Ig in binding buffer (final assay concentration <500 pM). (iii) 1.5 $\mu$l/well test compound or DMSO alone; (iv) 38 $\mu$l/well RPMI-8866 cell suspension (1.25×10$^6$ cells/well). The plates were incubated at room temperature for 45 minutes on a plate shaker at 200 rpm, filtered on a vacuum box, and washed on the same apparatus by the addition of 100 $\mu$L of binding buffer containing 1 mM MnCl$_2$. After insertion of the multiscreen plates into adapter plates (Packard, Meriden, Conn., cat# 6005178), 100 $\mu$L of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the IC$_{50}$ was determined from a ten point titration using a validated four parameter fit algorithm.

What is claimed is:

1. A compound having the formula I:

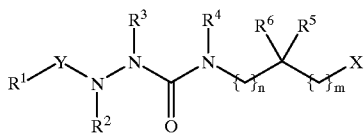

or a pharmaceutically acceptable salt thereof wherein:

R1 is

1) C1–10alkyl,
2) C2–10alkenyl,
3) C2–10alkynyl,
4) Cy,
5) Cy-C1–10alkyl,
6) Cy-C2–10alkenyl,
7) Cy-C2–10alkynyl, wherein alkyl, alkenyl, and alkynyl are optionally substituted with one to four substituents independently selected from $R^a$; and Cy is optionally substituted with one to four substituents independently selected from $R^b$;

$R^2$ and $R^3$ together with the atoms to which they are attached form a ring of 4 to 7 members containing 0–1 additional heteroatoms independently selected from oxygen, sulfur and nitrogen, wherein said ring may be isolated or benzo-fused, and optionally substituted with one to four substituents independently selected from $R^b$;

$R^4$ is 1) hydrogen,
2) $C_{1-10}$alkyl,
3) Cy, or
4) Cy-$C_{1-10}$alkyl;

wherein alkyl is optionally substituted with one to four substituents independently selected from $R^a$, and Cy is optionally substituted with one to four substituents independently selected from $R^b$;

$R^5$ is selected from the group consisting of 1) hydrogen,
2) $C_{1-10}$alkyl,
3) $C_{2-10}$alkenyl,
4) $C_{2-10}$alkynyl,
5) aryl,
6) aryl $C_{1-10}$alkyl,
7) heteroaryl, and
8) heteroaryl $C_{1-10}$alkyl, wherein alkyl, alkenyl and alkynyl are optionally substituted with one to four substituents independently selected from $R^a$, and aryl and heteroaryl are optionally substituted with one to four substituents independently selected from $R^b$;

$R^6$ is 1) hydrogen,
2) $C_{1-10}$alkyl,
3) $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl,
9) $Ar^1$—$Ar^2$—$C_{1-10}$alkyl,
10) $Ar^1$—$Ar^2$—$C_{2-10}$alkenyl,
11) $Ar^1$—$Ar^2$—$C_{2-10}$alkynyl,
12) $Ar^1$—$C_2$alkynyl-$Ar^2$—$C_{1-10}$alkyl,
13) $Ar^1$—$C_2$alkenyl-$Ar^2$—$C_{1-10}$alkyl,
14) $Ar^1$—$Ar^2$, wherein $Ar^1$ and $Ar^2$ are independently aryl or heteroaryl, and each is optionally substituted with one to four substituents independently selected from $R^b$; alkyl, alkenyl and alkynyl are optionally substituted with one to four substituents independently selected from $R^a$; and Cy is optionally substituted with one to four substituents independently selected from $R^b$ except aryl and heteroaryl;

$R^a$ is

1) —$CF_3$;
2) —$OR^d$,
3) —$NO_2$,
4) halogen
5) —$S(O)_m R^d$,
6) —$SR^d$,
7) —$S(O)_2 OR^d$,
8) —$S(O)_m NR^d R^e$,
9) —$NR^d R^e$,
10) —$O(CR^f R^g)_n NR^d R^e$,
11) —$C(O)R^d$,
12) —$CO_2 R^d$,
13) —$CO_2(CR^f R^g)_n CONR^d R^e$,
14) —$OC(O)R^d$,
15) —CN,
16) —$C(O)NR^d R^e$,
17) —$NR^d C(O)R^e$,
18) —$OC(O)NR^d R^e$,
19) —$NR^d C(O)OR^e$,
20) —$NR^d C(O)NR^d R^e$, or
21) —$CR^d(N$—$OR^e)$;

$R^b$ is 1) a group selected from $R^a$,
2) $C_{1-10}$ alkyl,
3) $C_{2-10}$ alkenyl,
4) $C_{2-10}$ alkynyl,
5) aryl $C_{1-10}$alkyl,
6) heteroaryl $C_{1-10}$ alkyl,
7) aryl, or
8) heteroaryl;

wherein alkyl, alkenyl, alkynyl, aryl, heteroaryl are optionally substituted with a group independently selected from $R^c$;

$R^c$ is 1) halogen,
2) amino,
3) carboxy,
4) $C_{1-4}$alkyl,
5) $C_{1-4}$alkoxy,
6) hydroxy,
7) aryl,
8) aryl $C_{1-4}$alkyl, or
9) aryloxy;

$R^d$ and $R^e$ are independently selected from the group consisting of 1) hydrogen,
2) $C_{1-10}$alkyl,
3) $C_{2-10}$alkenyl,
4) $C_{2-10}$alkynyl,
5) Cy, and
6) Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is 1) hydrogen,
2) $C_{1-10}$alkyl,
3) $C_{2-10}$alkenyl,
4) $C_{2-10}$alkynyl,
5) cyano,
6) aryl,
7) aryl $C_{1-10}$alkyl,
8) heteroaryl,
9) heteroaryl $C_{1-10}$alkyl, or
10) —$SO_2R^i$;

wherein alkyl, alkenyl, and alkynyl are optionally substituted with one to four substituents independently selected from $R^a$; and aryl and heteroaryl are each optionally substituted with one to four substituents independently selected from $R^b$;

$R^i$

1) $C_{1-10}$alkyl,
2) $C_{2-10}$alkenyl,
3) $C_{2-10}$alkynyl, or
4) aryl;

wherein alkyl, alkenyl, alkynyl and aryl are each optionally substituted with one to four substituents independently selected from $R^c$;

Cy is cycloalkyl, heterocyclyl, aryl, or heteroaryl;

m is an integer from 0 to 2;

n is an integer from 0 to 2;

X is

1) —$C(O)OR^d$,
2) —$P(O)(OR^d)(OR^e)$,
3) —$P(O)(R^d)(OR^e)$,
4) —$S(O)_mOR^d$,
5) —$C(O)NR^dR^h$,
6) -5-tetrazolyl, or
7) $CONHSO_2R^i$; and Y is 1) —C(O)—,
2) —O—C(O)—,
3) —$NR^e$—C(O)—,
4) —$S(O)_2$—,
5) —P(O)—
6) —C(O)C(O)—.

2. A compound of claim 1 wherein $R^1$ is

1) $C_{1-10}$alkyl,
2) Cy,
3) Cy-$C_{1-10}$alkyl, wherein alkyl is optionally substituted with one to four substituents independently selected from $R^a$; and Cy is optionally substituted with one to four substituents independently selected from $R^b$.

3. A compound of claim 1 wherein $R^2$ and $R^3$ together with the atoms to which they are attached form a ring of 5 to 6 members containing 0–1 additional heteroatoms independently selected from oxygen, sulfur and nitrogen, and wherein said ring is optionally substituted with one to four substituents independently selected from $R^b$.

4. A compound of claim 1 wherein $R^4$ is 1) hydrogen,
2) $C_{1-10}$alkyl, or
3) Cy—$C_{1-10}$alkyl.

5. A compound of claim 1 wherein $R^5$ is hydrogen;

$R^6$ is

1) $C_{1-10}$alkyl,
2) Cy,
3) Cy—$C_{1-10}$alkyl,
4) $Ar^1$–$Ar^2$,
5) $Ar^1$–$Ar^2$—$C_{1-10}$alkyl, wherein $Ar^1$ and $Ar^2$ are independently aryl or heteroaryl, and each is optionally substituted with one to four substituents independently selected from $R^b$; alkyl is optionally substituted with one to four substituents independently selected from $R^a$; and Cy is optionally substituted with one to four substituents independently selected from $R^b$ except aryl and heteroaryl.

6. A compound of claim 1 wherein

Y is —C(O)— or S(O)$_2$.

7. A compound of claim 1 having the formula Ia:

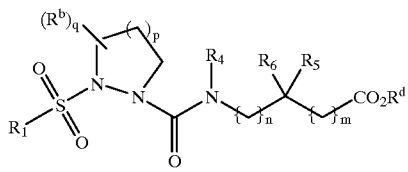

wherein $R^1$ is

1) $C_{1-10}$alkyl,
2) aryl,
3) heteroaryl,
4) aryl-$C_{1-10}$alkyl, or
5) heteroaryl-$C_{1-10}$alkyl, wherein alkyl is optionally substituted with one to four substituents independently selected from $R^a$; and aryl or heteroaryl is optionally substituted with one to four substituents independently selected from $R^b$;

$R^4$ is 1) hydrogen, or
2) $C_{1-10}$alkyl optionally substituted with one to four substituents independently selected from $R^a$;

$R^5$ is hydrogen;

$R^6$ is

1) $C_{1-10}$alkyl,
2) aryl,
3) heteroaryl,
4) aryl-$C_{1-10}$alkyl,
5) heteroaryl-$C_{1-10}$alkyl,
6) $Ar^1$–$Ar^2$, or
7) $Ar^1$–$Ar^2$—$C_{1-10}$alkyl, wherein alkyl is optionally substituted with one to four substituents independently selected from $R^a$; aryl or heteroaryl is optionally substituted with one to four substituents independently selected from $R^b$ except aryl and heteroaryl; $Ar^1$ and $Ar^2$ are independently aryl or heteroaryl, and each is optionally substituted with from one to four groups independently selected from $R^b$;

$R^d$ is 1) hydrogen,
2) $C_{1-10}$alkyl,
3) Cy, and
4) Cy $C_{1-10}$alkyl, wherein alkyl and Cy are optionally substituted with one to four substituents independently selected from $R^c$;

p is 1 or 2;

q is 0 to 4;

n and m are independently 0 or 1, and n+m=0 or 1;

$R^a$, $R^b$, $R^c$ and Cy are as defined in claim 1.

8. A compound of claim 7 wherein $R^1$ is aryl optionally substituted with one to four halogen;

$R^4$ is hydrogen;

$R^5$ is hydrogen;

$R^6$ is

1) $C_{1-5}$alkyl,
2) aryl,
3) aryl-$C_{1-5}$alkyl,
4) $Ar^1$–$Ar^2$, or
5) $Ar^1$–$Ar^2$—$C_{1-5}$alkyl, wherein alkyl is optionally substituted with one to four substituents independently selected from $R^a$; aryl is optionally substituted with one to four substituents independently selected from $R^b$ except aryl and heteroaryl; $Ar^1$ and $Ar^2$ are independently phenyl, and each is optionally substituted with from one to four groups independently selected from $R^b$.

9. A compound of claim 1 having the formula:

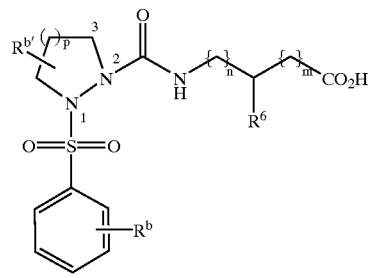

| n/m/p | $R^{b'}$ | $R^b$ | $R^6$ |
|---|---|---|---|
| 0/0/1 | H | H | (S)-2-methylpropyl |
| 0/0/1 | H | 3,5-dichloro | (S)-2-naphthylmethyl |
| 0/0/1 | (3R)-methyl | 3,5-dichloro | (S)-benzyl |
| 0/0/1 | (3S)-methyl | 3,5-dichloro | (S)-benzyl |
| 0/0/1 | 5-methyl | 3,5-dichloro | (S)-benzyl |
| 0/0/2 | H | 3,5-dichloro | (S)-4-fluorobenzyl |
| 0/0/2 | H | 3-fluoro | (S)-4-fluorobenzyl |
| 0/0/1 | H | 3,5-dichloro | (S)-benzyl |
| 0/0/1 | H | 4-fluoro | (S)-n-butyl |
| 0/0/1 | H | 4-fluoro | phenyl |
| 0/0/1 | H | 4-fluoro | (S)-4'-biphenylmethyl |
| 0/1/1 | H | 4-fluoro | methyl |
| 0/1/1 | H | 4-fluoro | benzyl |
| 0/1/1 | H | 4-fluoro | 2-methylpropyl |
| 0/1/1 | H | 4-fluoro | phenyl |

-continued

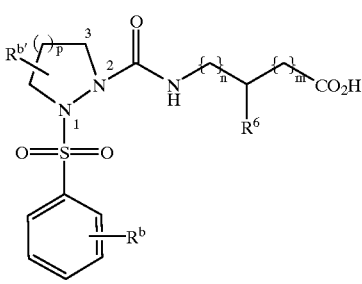

| n/m/p | R$^{b'}$ | R$^b$ | R$^6$ |
|---|---|---|---|
| 1/0/1 | H | 4-fluoro | methyl |
| 0/0/1 | H | 4-fluoro | (S)-benzyl |
| 0/0/1 | H | 3-fluoro | (S)-4-fluorobenzyl |
| 0/0/1 | H | 3-fluoro | (S)-4-(2'-CN-phenyl)benzyl |
| 0/0/1 | H | 3,5-dichloro | (S)-4-(2'-CH$_3$O-phenyl)benzyl |

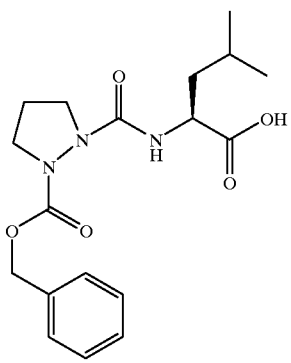

; or

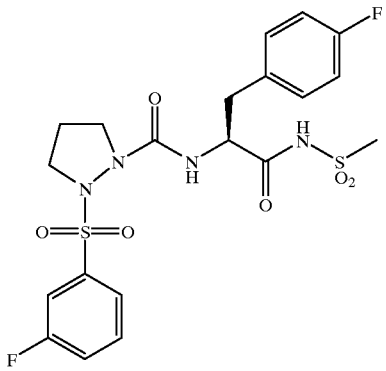

10. A pharmaceutical composition comprising a compound of claim 1 and a pharmaceutically acceptable carrier.

11. A method for inhibiting cell adhesion in a mammal which comprises administering to said mammal an effective amount of a compound of claim 1.

12. A method for the treatment of diseases, disorders, conditions or symptoms mediated by cell adhesion in a mammal which comprises administering to said mammal a therapeutically effective amount of a compound of claim 1.

13. A method for treating asthma in a mammal comprising administering to said mammal a therapeutically effective amount of a compound of claim 1.

14. A method for treating multiple sclerosis in a mammal comprising administering to said mammal a therapeutically effective amount of a compound of claim 1.

15. A method for treating inflammatory bowel disorders in a mammal comprising administering to said mammal a therapeutically effective amount of a compound of claim 1.

16. A method for treating allergic rhinitis in a mammal comprising administering to said mammal a therapeutically effective amount of a compound of claim 1.

17. A method for the treatment of atherosclerosis in a mammal which comprises administering to said mammal a therapeutically effective amount of a compound of claim 1.

18. A method for the treatment of inflammation in a mammal which comprises administering to said mammal an effective amount of a compound of claim 1.

19. A method for inhibiting cell adhesion in a mammal which comprises administering to said mammal an effective amount of a compound of claim 2.

20. A method for the treatment of diseases, disorders, conditions or symptoms mediated by cell adhesion in a mammal which comprises administering to said mammal a therapeutically effective amount of a compound of claim 2.

21. A method for the treatment of asthma, allergic rhinitis, multiple sclerosis, inflammatory bowel diseases, atherosclerosis or inflammation in a mammal which comprises administering to said mammal a therapeutically effective amount of a compound of claim 2.

22. A pharmaceutical composition which comprises a compound of claim 2 and a pharmaceutically acceptable carrier thereof.

* * * * *